United States Patent
Palomino Laria et al.

(10) Patent No.: US 12,384,754 B2
(45) Date of Patent: Aug. 12, 2025

(54) COCRYSTALS OF (1R,3S)-3-(5-CYANO-4-PHENYL-1,3-THIAZOL-2-YLCARBAMOYL) CYCLOPENTANE CARBOXYLIC ACID

(71) Applicant: PALOBIOFARMA, S.L., Barcelona (ES)

(72) Inventors: Julio Castro Palomino Laria, Barcelona (ES); Juan Camacho Gómez, Barcelona (ES)

(73) Assignee: PALOBIOFARMA, S.L., Barcelona (ES)

( * ) Notice: Subject to any disclaimer, the term of this patent is extended or adjusted under 35 U.S.C. 154(b) by 539 days.

(21) Appl. No.: 17/906,367

(22) PCT Filed: Mar. 15, 2021

(86) PCT No.: PCT/EP2021/056506
§ 371 (c)(1),
(2) Date: Sep. 15, 2022

(87) PCT Pub. No.: WO2021/185748
PCT Pub. Date: Sep. 23, 2021

(65) Prior Publication Data
US 2023/0183195 A1    Jun. 15, 2023

(30) Foreign Application Priority Data
Mar. 16, 2020  (EP) .................................. 20382194

(51) Int. Cl.
| | |
|---|---|
| *C07D 277/56* | (2006.01) |
| *A61K 45/06* | (2006.01) |
| *C07C 65/05* | (2006.01) |
| *C07C 275/02* | (2006.01) |
| *C07D 213/82* | (2006.01) |

(52) U.S. Cl.
CPC ............ *C07D 277/56* (2013.01); *A61K 45/06* (2013.01); *C07C 65/05* (2013.01); *C07C 275/02* (2013.01); *C07D 213/82* (2013.01); *C07B 2200/13* (2013.01)

(58) Field of Classification Search
CPC .... C07D 277/56; C07D 213/82; A61K 45/06; A61K 31/426; C07C 65/05; C07C 275/02; C07B 2200/13
See application file for complete search history.

(56) References Cited

FOREIGN PATENT DOCUMENTS

| WO | WO 2009/044250 A1 | 4/2009 |
| WO | WO 2011/158110 A2 | 12/2011 |
| WO | WO 2018/162505 A1 | 9/2018 |

OTHER PUBLICATIONS

Hasko et al., Adenosine receptors: therapeutic aspects for inflammatory and immune diseases. Nat Rev Drug Discov. Sep. 2008;7(9):759-70.
Hocher. Adenosine A1 receptor antagonists in clinical research and development. Kidney Int. Sep. 2010;78(5):438-45.
Izutsu et al., Characterization and Quality Control of Pharmaceutical Cocrystals. Chem Pharm Bull (Tokyo). Oct. 1, 2016;64(10):1421-1430.
Regulatory Classification of Pharmaceutical Co-Crystals Guidance for Industry, U.S. Department of Health and Human Services. http://www.fda.gov/Drugs/GuidanceComplianceRegulatoryInformation/Guidances/default.htm. Feb. 2018. 7 pages.

*Primary Examiner* — Clinton A Brooks
*Assistant Examiner* — Kyle Nottingham
(74) *Attorney, Agent, or Firm* — Casimir Jones, S.C.; Tristan A. Fuierer

(57) ABSTRACT

The present invention relates to the cocrystals of (1R,3S)-3-(5-cyano-4-phenyl-1,3-thiazol-2-ylcarbamoyl) cyclopentane carboxylic acid, a process for obtaining said cocrystals, combination products and pharmaceutical compositions comprising said cocrystals and their medical uses, in particular for the treatment or prevention of diseases known to ameliorate by $A_1$ adenosine receptor antagonism.

20 Claims, 8 Drawing Sheets

COCRYSTALS OF (1R,3S)-3-(5-CYANO-4-PHENYL-1,3-THIAZOL-2-YLCARBAMOYL)CYCLOPENTANE CARBOXYLIC ACID

CROSS-REFERENCE TO RELATED APPLICATIONS

This application is filed under the provisions of 35 U.S.C. § 371 and claims the priority of International Patent Application No. PCT/EP2021/056506 filed on 15 Mar. 2021 entitled "Cocrystals of (1R,3S)-3-(5-cyano-4-phenyl-1,3-thiazol-2-ylcarbamoyl) cyclopentane carboxylic acid" in the name of Julio Castro PALOMINO LARIA, et al., which claims priority to European Patent Application No. 20382194.7, filed on 16 Mar. 2020, both of which are hereby incorporated by reference herein in their entirety.

FIELD OF INVENTION

The present invention is related to new cocrystals of (1R,3S)-3-(5-cyano-4-phenyl-1,3-thiazol-2-ylcabamoyl)cyclopentane carboxylic acid, which is an adenosine $A_1$ adenosine receptor antagonist. Said cocrystals are useful for the treatment or prevention of diseases known to be ameliorated by antagonism of the $A_1$ adenosine receptor.

BACKGROUND OF INVENTION

Adenosine $A_1$ receptor antagonists are useful for the treatment or prevention of various diseases including hypertension, heart failure, ischemia, supraventricular arrhythmia, acute renal failure, myocardial reperfusion injury, asthma, allergic reactions including rhinitis and urticaria, scleroderma and autoimmune diseases, such as multiple sclerosis. (Hocher, B, *Adenosine A1 receptor antagonists in clinical research and development*, Kidney International (2010) 78, 438-445; Haskó, G et al, *Adenosine receptors: therapeutic aspects for inflammatory and immune diseases*, Nature Reviews, volume 7, September 2008, 759).

Specifically, patent application WO 2009/044250 A1 discloses 5-cyano-1,3-thiazole derivatives, which are potent $A_1$ adenosine receptor antagonists, and which are useful in the treatment of the above-mentioned diseases. In said patent application, 3-(5-cyano-4-phenyl-1,3-thiazol-2-ylcarbamoyl) cyclopentane carboxylic acid is disclosed, in particular the (1R,3S) stereoisomer, whose structure is shown below:

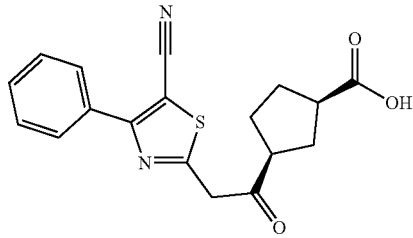 [SMILES: N#Cc1sc(CC(=O)[C@H]2CC[C@@H](C(=O)O)C2)nc1-c1ccccc1]

Cocrystals of 5-cyano-1,3-thiazole derivatives are not mentioned in the cited document, nor in other documents known to the applicant.

Although (1R,3S)-3-(5-cyano-4-phenyl-1,3-thiazol-2-ylcarbamoyl) cyclopentane carboxylic acid has shown suitable pharmacological activity, there seems to be room for improvement of the physical and/or pharmacological properties of said compound, in particular, its hygroscopicity and its bioavailabilty. Improvement in said properties would assist further pharmaceutical development into a medicament.

Therefore, there is a need in the art to provide a method for improving the hygroscopicity and/or the bioavailability of (1R,3S)-3-(5-cyano-4-phenyl-1,3-thiazol ylcarbamoyl) cyclopentane carboxylic acid.

Therefore, the development of soluble and stable pharmaceutically acceptable forms of said (1R,3S)-3-(5-cyano-4-phenyl-1,3-thiazol-2-ylcarbamoyl) cyclopentane carboxylic acid with improved hygroscopicity and/or the bioavailability is highly desirable. The present invention addresses such concerns.

Cocrystals are distinguished from salts because unlike salts, the components that co-exist in the cocrystal lattice with a defined stoichiometry interact nonionically. Generally, it is considered that when an active pharmaceutical ingredient (API) and its cocrystal forming compound (co-former) have a $\Delta pKa$ ($\Delta pKa=pKa$ (conjugate acid of base)-$pKa$ (acid))<1, there will be less than substantial proton transfer. If this criterion is met, the API-coformer entity should be classified as a cocrystal. (Regulatory Classification of Pharmaceutical Co-Crystals Guidance for Industry, February 2018, http://www.fda.gov/Drugs/GuidanceComplianceRegulatotyInformation/Guidances/default.htm).

Several properties can be altered by cocrystal formation, such as melting point, considered one of the first physicochemical properties to be in account, storage stability, solubility, dissolution rate, hygroscopicity and bioavailability, among others. (Izutsu, K et al, *Characterization and Quality Control of Pharmaceutical Cocrystals*, Chem. Pharm. Bull. 64, 1421-1430 (2016)).

Given the availability of a large number of pharmaceutically acceptable coformers and the lack of correlation between the nature of a pharmaceutically acceptable coformer and the final properties of the corresponding cocrystal, finding appropriate cocrystals is a difficult process, and its results are, a priori, unpredictable.

There is a need to provide cocrystals which improve the physicochemical and pharmaceutical properties of (1R,3S)-3-(5-cyano-4-phenyl-1,3-thiazol-2-ylcarbamoyl) cyclopentane carboxylic acid, in particular cocrystals which improve hygroscopicity, without negatively affecting other important parameters, such as crystallinity or bioavailability of active compound. In particular, it is necessary to reduce the hygroscopicity of (1R,3S)-3-(5-cyano-4-phenyl-1,3-thiazol-2-ylcarbamoyl) cyclopentane carboxylic acid under usual conditions of drug storage (<75% RH), and at the same time ensuring good levels of stability and solubility thereof, to obtain an improvement in the production, handling, storage and pharmaceutical properties of said acid.

SUMMARY OF INVENTION

The present invention provides cocrystals of (1R,3S)-3-(5-cyano-4-phenyl-1,3-thiazol-2-ylcarbamoyl) cyclopentane carboxylic acid.

After trying to obtain cocrystals of (1R,3S)-3-(5-cyano-4-phenyl-1,3-thiazol-2-ylcarbamoyl) cyclopentane carboxylic acid with a high number of potential crystal forming compounds, the inventors have surprisingly found that gentisic acid, urea and nicotinamide exhibit particularly good properties of hygroscopicity and bioavailability and higher melting points, with respect to compound in free acid form. The improvement in the aforementioned properties implies an advantage for the processes of production, handling and storage of said compound as well as in pharmaceutical characteristics of said product. Specifically, a significant improvement in oral bioavailability has been shown by cocrystals object of the present invention, which will enable the administration of significant lower doses of the compound to achieve the target therapeutic levels.

In connection with the subject matter of the present invention, no disclosure is known in state of the art relating to the preparation and use of any cocrystal of a compound belonging to the family of compounds disclosed in patent application WO 2009/044250 A1, much less cocrystals of (1R,3S)-3-(5-cyano-4-phenyl-1,3-thiazol-2-ylcarbamoyl) cyclopentane carboxylic acid and even less the cocrystals with gentisic acid, urea and nicotinamide.

Thus, in a first aspect, the present invention relates to the cocrystals of (1R,3S)-3-(5-cyano-4-phenyl-1,3-thiazol-2-ylcarbamoyl) cyclopentane carboxylic acid with a cocrystal forming compound selected from the group consisting of gentisic acid, urea and nicotinamide.

In a second aspect, the present invention relates to a process for the preparation of the cocrystal defined in the first aspect, comprising:
a) putting into contact (1R,3S)-3-(5-cyano-4-phenyl-1,3-thiazol ylcarbamoyl) cyclopentane carboxylic acid and a cocrystal forming compound selected from the group consisting of gentisic acid, urea and nicotinamide, in the presence of a liquid, and
b) isolating the resulting cocrystal.

In a third aspect, the present invention relates to a combination product comprising the cocrystal according to the first aspect and one or more therapeutic agents selected from the group consisting of angiotensin converting enzyme inhibitors (ACE-inhibitors), angiotensin receptor antagonists, statins, beta-blockers, calcium antagonists and diuretics.

In a fourth aspect, the present invention relates to a pharmaceutical composition comprising the cocrystal according to the first aspect or the combination product according to third aspect and a pharmaceutically acceptable excipient.

In a fifth aspect, the present invention relates to the cocrystal according to first aspect, the combination product according to the third aspect or the pharmaceutical composition according to the fourth aspect, for use as a medicament.

In a sixth aspect, the present invention relates to the cocrystal according to the first aspect, the combination product according to the third aspect or the pharmaceutical composition according to the fourth aspect, for use in the treatment and/or prevention of a disease known to ameliorate by $A_1$ adenosine receptor antagonism.

DETAILED DESCRIPTION OF INVENTION

Figure 1:
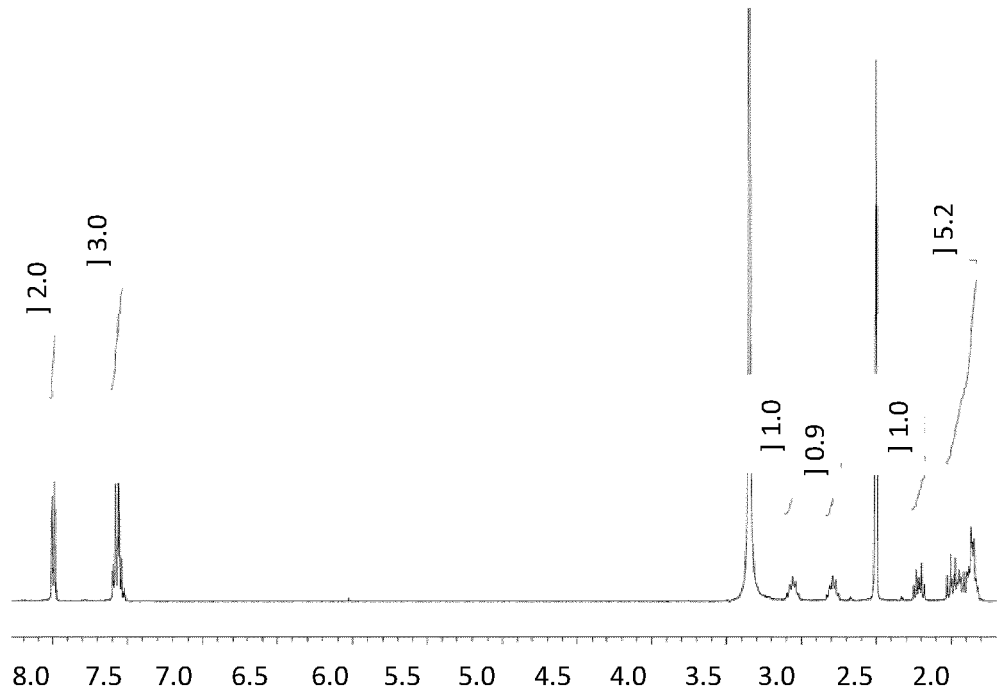
FIG. 1 illustrates $^1$H NMR spectrum of (1R,3S)-3-(5-cyano-4-phenyl-1,3-thiazol-2-ylcarbamoyl) cyclopentane carboxylic acid.

The present patent application discloses several cocrystals of (1R,3S)-3-(5-cyano-4-phenyl-1,3-thiazol-2-ylcarbamoyl) cyclopentane carboxylic acid. The following cocrystals have been obtained from (1R,3S)-3-(5-cyano-4-phenyl-1,3-thiazol-2-ylcarbamoyl) cyclopentane carboxylic acid and a cocrystal forming compound selected from the group consisting of gentisic acid, urea and nicotinamide. All of them have shown improved physicochemical and pharmacokinetics properties with respect to the free acid.

Gentisic Acid Cocrystal

Inventors have surprisingly found that the cocrystal of (1R,3S)-3-(5-cyano-4-phenyl-1,3-thiazol-2-ylcarbamoyl)

cyclopentane carboxylic acid and gentisic acid, has the following advantageous properties:
1) Stability under forced conditions (one week) and in 4-weeks stability assay: no crystallinity changes, colour or any other change in the aspect were observed in obtained cocrystal.
2) Hygroscopicity: it shows less hygroscopicity than the free acid, particularly in the usual storage conditions of drugs (<75% RH).
3) Bioavailability: It has been surprising the improvement of the gentisic acid cocrystal in the oral exposure and bioavailability compared to the free acid.

Therefore, said gentisic acid cocrystal offers advantages for the preparation of solid dosage forms, containing the pharmacologically active compound, facilitating its manipulation and allowing a better dosage regimen. In addition, the gentisic acid cocrystal object of the present invention is a stable solid, even under forced stability conditions. This cocrystal is less hygroscopic than free acid, specially up to 75% RH, as it can be seen in the examples when comparing the variation in the moisture content reached by the gentisic acid cocrystal (0.10% at 75% RH) with that of the free acid (0.43% at 75% RH).

Urea Cocrystal

The cocrystal of (1R,3S)-3-(5-cyano-4-phenyl-1,3-thiazol-2-ylcarbamoyl) cyclopentane carboxylic acid with urea was also prepared and found to have all the following advantages:
1) Stability under forced conditions (one week) and in 4-weeks stability assay: no crystallinity changes, colour or any other change in the aspect were observed in obtained cocrystal.
2) Hygroscopicity: it shows less hygroscopicity than the free acid, particularly in the usual storage conditions of drugs (<75% RH).
3) Bioavailability: It has been surprising has been the improvement of the urea cocrystal in the oral exposure and bioavailability compared to the free acid.

Therefore, said urea cocrystal offers advantages for the preparation of solid dosage forms, containing the pharmacologically active compound, facilitating its manipulation and allowing a better dosage regimen. In addition, the urea cocrystal object of the present invention is a stable solid, even under forced stability conditions. This cocrystal is less hygroscopic than free acid, specially up to 75% RH, as it can be seen in the examples when comparing the variation in the moisture content reached by the urea cocrystal (0.08% at 75% RH) with that of the free acid (0.43% at 75% RH).

Nicotinamide Cocrystal

Inventors have surprisingly found that the cocrystal of (1R,3S)-3-(5-cyano-4-phenyl-1,3-thiazol-2-ylcarbamoyl) cyclopentane carboxylic acid with nicotinamide, has all the following advantages:
1) Stability under forced conditions (one week) and in 4-weeks stability assay: no crystallinity changes, colour or any other change in the aspect were observed in obtained cocrystal during both stability assays.
2) Hygroscopicity: it shows less hygroscopicity than the free acid, particularly in range between 5-70% RH.
3) Bioavailability: It has been surprising has been the improvement of the nicotinamide cocrystal in the oral exposure and bioavailability compared to the free acid.

Therefore, said nicotinamide cocrystal offers advantages for the preparation of solid dosage forms, containing the pharmacologically active compound, facilitating its manipulation and allowing a better dosage regimen. In addition, the nicotinamide cocrystal object of the present invention is a stable solid, even under forced stability conditions. This cocrystal is less hygroscopic than free acid, specially in range between 5-70% RH, as it can be seen in the examples when comparing the variation in the moisture content reached by the nicotinamide cocrystal.

As shown in examples 5 to 8, the obtained cocrystals show an improvement in melting point, hygroscopicity and bioavailability properties with respect to the free acid.

Therefore, the first aspect of the present invention is addressed to the cocrystals of (1R,3S)-3-(5-cyano-4-phenyl-1,3-thiazol-2-ylcarbamoyl) cyclopentane carboxylic acid with a cocrystal forming compound selected from the group consisting of gentisic acid, urea and nicotinamide.

In the context of the present invention the term "cocrystal" is used to designate a crystalline material composed of two or more different molecules in a defined stoichiometric ratio within the same crystal lattice, which interact through nonionic and noncovalent bonds. Generally, cocrystals are composed of an API moiety such as (1R,3S)-3-(5-cyano-4-phenyl-1,3-thiazol-2-ylcarbamoyl) cyclopentane carboxylic acid and cocrystal forming compound (coformer, cocrystal former, guest molecule).

In the context of the present invention the term "cocrystal forming compound" or "coformer" is used to designate a component that is typically solid at room temperature and which interacts nonionically with the API in the crystal lattice.

In the context of the present invention a liquid is any substance which is liquid at room temperature, for example at 25° C., preferably a class 1, class 2 or class 3 solvent according to ICH guideline Q3C (R6) being, preferably, selected from the group consisting of water, methanol, ethanol, isopropanol, propanol, butanol, acetonitrile, ethyl acetateo de etilo, i-butyl acetate, propan-2-one (acetone), methyl-isobuthyl-cetone (MIBK), tetrahyidrofurane (THF), 1,4-dioxane, dichloromethane (DCM), p-xylene, ethyl ether, methyl tert-butyl ether (TMBE) and heptane.

In a preferred embodiment, the cocrystal is a cocrystal of (1R,3S)-3-(5-cyano-4-phenyl-1,3-thiazol-2-ylcarbamoyl) cyclopentane carboxylic acid and gentisic acid.

In more preferred embodiment, the molar ratio of (1R,3S)-3-(5-cyano-4-phenyl-1,3-thiazol-2-ylcarbamoyl) cyclopentane carboxylic acid to gentisic acid in said cocrystal is comprised between 0.9 and 1.1, preferably 1:1.

In more preferred embodiment, the cocrystal of (1R,3S)-3-(5-cyano-4-phenyl-1,3-thiazol-2-ylcarbamoyl) cyclopentane carboxylic acid and gentisic acid has a differential scanning calorimetry (DSC) thermogram comprising an endothermic peak at about 181.69° C.

In more preferred embodiment, the cocrystal of (1R,3S)-3-(5-cyano-4-phenyl-1,3-thiazol-2-ylcarbamoyl) cyclopentane carboxylic acid and gentisic acid is characterized by showing an X-ray powder diffraction pattern comprising 2θ° peaks at 6.99, 13.29, 13.42, 14.02, 17.82 (all of them ±0.20) 2θ°, wherein the X-ray diffraction pattern is measured using a CuKα radiation. In a more preferred embodiment, the X-ray diffraction pattern comprises 2θ° peaks at 6.99, 13.29, 13.42, 14.02, 17.82, 18.71, 21.09, 26.34, 26.58, 27.28, 28.24, 31.56 (all of them ±0.20) 2θ°.

In another preferred embodiment, the cocrystal is a cocrystal of (1R,3S)-3-(5-cyano-4-phenyl-1,3-thiazol-2-ylcarbamoyl) cyclopentane carboxylic acid and urea.

In more preferred embodiment, the molar ratio of (1R,3S)-3-(5-cyano-4-phenyl-1,3-thiazol-2-ylcarbamoyl) cyclopentane carboxylic acid to urea in said cocrystal is comprised between 0.9 and 1.1, preferably 1:1.

In more preferred embodiment, the cocrystal of (1R,3S)-3-(5-cyano-4-phenyl-1,3-thiazol-2-ylcarbamoyl) cyclopentane carboxylic acid and urea has a differential scanning calorimetry (DSC) thermogram comprising an endothermic peak at about 197.7° C.

In more preferred embodiment, the cocrystal of (1R,3S)-3-(5-cyano-4-phenyl-1,3-thiazol-2-ylcarbamoyl) cyclopentane carboxylic acid and urea is characterized by showing an X-ray powder diffraction pattern comprising 2θ° peaks at 8.32, 8.82, 13.86, 15.60, 16.47, 24.86 (all of them ±0.20) 2θ°, wherein the X-ray diffraction pattern is measured using a CuKα radiation. In a more preferred embodiment, the X-ray diffraction pattern comprises 2θ° peaks at 7.77, 8.32, 8.82, 13.86, 15.60, 16.47, 18.23, 18.94, 19.38, 19.86, 20.05, 20.71, 21.38, 21.84, 22.76, 23.02, 24.86, 26.10, 27.28, 28.40 (all of them ±0.20) 2θ°.

In a preferred embodiment, the cocrystal is a cocrystal of (1R,3S)-3-(5-cyano-4-phenyl-1,3-thiazol-2-ylcarbamoyl) cyclopentane carboxylic acid and nicotinamide.

In more preferred embodiment, the molar ratio of (1R,3S)-3-(5-cyano-4-phenyl-1,3-thiazol-2-ylcarbamoyl) cyclopentane carboxylic acid to nicotinamide cocrystal is comprised between 0.9 and 1.1, preferably 1:1.

In more preferred embodiment, the cocrystal of (1R,3S)-3-(5-cyano-4-phenyl-1,3-thiazol-2-ylcarbamoyl) cyclopentane carboxylic acid and nicotinamide has a differential scanning calorimetry (DSC) thermogram comprising an endothermic peak at about 189.55° C.

In more preferred embodiment, the cocrystal of (1R,3S)-3-(5-cyano-4-phenyl-1,3-thiazol-2-ylcarbamoyl) cyclopentane carboxylic acid and nicotinamide is characterized by showing an X-ray powder diffraction pattern comprising 2θ° peaks at 6.40, 8.54, 11.75, 17.29, 20.88, 23.66 (all of them ±0.20) 2θ°, wherein the X-ray diffraction pattern is measured using a CuKα radiation. In a more preferred embodiment, the X-ray diffraction pattern comprises 2θ° peaks at 6.40, 8.54, 11.28, 11.75, 13.02, 17.29, 18.33, 19.56, 20.11, 20.55, 20.88, 21.36, 21.62, 22.73, 22.96, 23.66, 24.26, 24.46, 25.12, 26.17, 26.46, 27.53, 28.81, 29.36, 30.28, 32.96 (all of them ±0.20) 2θ°.

In the present invention (1R,3S)-3-(5-cyano-4-phenyl-1,3-thiazol-2-ylcarbamoyl) cyclopentane carboxylic acid has a pKa of 4.3. The ΔpKa between the free acid and the selected cocrystal forming compounds is <1, as is shown in the following table 1.

TABLE 1

| Compound | pKa conjugated base | ΔpKa |
| --- | --- | --- |
| Gentisic acid | Not basic | — |
| Urea | Not basic | — |
| Nicotinamide | 3.4 | 0.9 |

General Process of Preparation of (1R,3S)-3-(5-Cyano-4-Phenyl-1,3-Thiazol-2-Ylcarbamoyl)Cyclopentane Carboxylic Acid Cocrystals In another aspect, the present invention is referred a process for the preparation of the (1R,3S)-3-(5-cyano-4-phenyl-1,3-thiazol-2-ylcarbamoyl) cyclopentane carboxylic acid cocrystals object of the present invention, comprising:

a) putting into contact (1R,3S)-3-(5-cyano-4-phenyl-1,3-thiazol ylcarbamoyl) cyclopentane carboxylic acid and crystal forming compound in presence of a liquid, and b) isolating the (1R,3S)-3-(5-cyano-4-phenyl-1,3-thiazol-2-ylcarbamoyl) cyclopentane carboxylic acid-coformer cocrystal.

Step a) comprises putting into contact (1R,3S)-3-(5-cyano-4-phenyl-1,3-thiazol ylcarbamoyl) cyclopentane carboxylic acid and the crystal forming compound selected from gentisic acid, urea and nicotinamide in presence of a liquid. In an embodiment, putting into contact the two starting compounds can be made by mixing them. In an embodiment, the mixture resulting from step a) may be seeded with small crystals of the desired cocrystal compound to facilitate precipitation although this is not essential to obtain the cocrystals.

(1R,3S)-3-(5-cyano-4-phenyl-1,3-thiazol-2-ylcarbamoyl) cyclopentane carboxylic acid is prepared using the processes disclosed in patent application WO 2009/044250A1, incorporated by reference to the present document.

In a particular embodiment, when the cocrystal forming compound is gentisic acid, in step a) the (1R,3S)-3-(5-cyano-4-phenyl-1,3-thiazol-2-ylcarbamoyl) cyclopentane carboxylic acid and the gentisic acid are in molar ratio of 0:9 to 1:1.5, preferably 1:1 to 1:1.5, preferably 1:1 to 1:1.2. Putting into contact the two starting compounds can be made by mixing them. The mixture of both compounds can be carried out, for example, by magnetic stirring. The mixture may be a solution or a suspension. Preferably step a) comprises preparing the mixture of acid and gentisic acid to the reflux temperature of the liquid forming part of the solution or suspension, preferably until a solution is obtained. In a particular embodiment, the mixture is maintained, preferably at reflux temperature and with stirring, between 30 minutes and 24 hours, more preferably between 5 hours and 18 hours, still more preferably between 10 hours and 15 hours.

The liquid may be any suitable liquid which does not react with (1R,3S)-3-(5-cyano-4-phenyl-1,3-thiazol-2-ylcarbamoyl) cyclopentane carboxylic acid or with gentisic acid. Preferably, the liquid is selected from the group consisting of alkanols, aliphatic hydrocarbons, aromatic hydrocarbons, ethers, ketones, esters, dichloromethane, chloroform, di methylsulfoxide, acetonitrile, water and mixtures thereof, preferably water, acetonitrile, methanol, isopropanol, ethyl acetate, acetona, methyl isobutyl ketone, methyl tert-butyl ether, tetrahydrofuran, dioxane, dichloromethane, xylene, heptane and mixtures thereof.

In another particular embodiment, when the cocrystal forming compound is urea, in step a) the (1R,3S)-3-(5-cyano-4-phenyl-1,3-thiazol-2-ylcarbamoyl) cyclopentane carboxylic acid and urea are in molar ratio of 0.9:1 to 1:1.5, preferably 1:1 to 1:1.5, preferably 1:1 to 1:1.2. Putting into contact the two starting compounds can be made by mixing them. The mixture of both compounds can be carried out, for example, by magnetic stirring.

The mixture may be a solution or a suspension. Preferably step a) comprises preparing the mixture of acid and urea to the reflux temperature of the liquid forming part of the solution or suspension, preferably until a solution is obtained. In a particular embodiment, the mixture is maintained, preferably at reflux temperature and with stirring, between 30 minutes and 24 hours, more preferably between 5 hours and 18 hours, still more preferably between 10 hours and 15 hours.

The liquid may be any suitable liquid which does not react with (1R,3S)-3-(5-cyano-4-phenyl-1,3-thiazol-2-ylcarbamoyl) cyclopentane carboxylic acid or with urea. Preferably, the liquid is selected from the group consisting of alkanols, aliphatic hydrocarbons, aromatic hydrocarbons, ethers, ketones, esters, dichloromethane, chloroform, dimethylsulfoxide, acetonitrile, water and mixtures thereof, preferably acetonitrile, methanol, isopropanol, isobutyl acetate, acetona, methyl isobutyl ketone, dichloromethane, xylene, heptane and mixtures thereof.

In a particular embodiment, when the cocrystal forming compound is nicotinamide, in step a) the (1R,3S)-3-(5-cyano-4-phenyl-1,3-thiazol-2-ylcarbamoyl) cyclopentane carboxylic acid and nicotinamide are in molar ratio of 0:9 to 1:1.5, preferably 1:1 to 1:1.5, preferably 1:1 to 1:1.2. Putting into contact the two starting compounds can be made by mixing them. The mixture of both compounds can be carried out, for example, by magnetic stirring. The mixture may be a solution or a suspension. Preferably step a) comprises preparing the mixture of acid and nicotinamide to the reflux temperature of the liquid forming part of the solution or suspension, preferably until a solution is obtained. In a particular embodiment, the mixture is maintained, preferably at reflux temperature and with stirring, between 30 minutes and 24 hours, more preferably between 5 hours and 18 hours, still more preferably between 10 hours and 15 hours.

The liquid may be any suitable liquid which does not react with (1R,3S)-3-(5-cyano-4-phenyl-1,3-thiazol-2-ylcarbamoyl) cyclopentane carboxylic acid or with nicotinamide. Preferably, the liquid is selected from the group consisting of alkanols, aliphatic hydrocarbons, aromatic hydrocarbons, ethers, ketones, esters, dichloromethane, chloroform, dimethylsulfoxide, acetonitrile, water and mixtures thereof, preferably acetonitrile, acetone, methyl isobutyl ketone and mixtures thereof.

As used herein, the term alkyl includes linear or branched hydrocarbon chains, having from 1 to 12 carbon atoms, preferably from 1 tp 6 carbon atoms, and no having insaturations. When the term alkyl is accompanied by an expression indicating the number of carbon atoms, such as $C_1$-$C_3$, it means that said alkyl has the indicated number of carbon atoms, such as from 1 to 3 carbon atoms.

As used herein, the term alkanol includes linear or branched alkyl chains as have been previously defined, linked to a hydroxyl group (OH). Preferred alkanols are isopropanol, propanol, ethanol, methanol, butanol, tert-butanol, isobutanol and mixtures thereof, more preferably isopropanol, propanol, ethanol, methanol and mixtures thereof.

As used herein, the term aliphatic hydrocarbons refer to compounds consisting of carbon and hydrogen atoms, saturated or with one or more insaturations (double or triple bond), for example, one, two or three insaturations, linear, branched or cyclic; preferably having 5 to 12 carbon atoms, more preferably 5 to 8 carbon atoms, and still more preferably 6 or 7 carbon atoms. Examples of aliphatic hydrocarbons are penthane, hexane, heptane, cyclopentane, cyclohexane, and mixtures thereof, among others, preferably heptane and cyclohexane and mixtures thereof.

As used herein, the term aromatic hydrocarbons refer to cyclic compounds consisting of carbon and hydrogen atoms, unsaturated, and complying with Hückel rule, preferably having 6 carbon atoms in the cycle, optionally substituted by one, two or three $C_1$-$C_3$ alkyl groups which may be the same or different. Examples of aromatic hydrocarbons are toluene and xylene and mixtures thereof.

As used herein, the term ether refers to compounds of formula R—O—R', wherein R and R' are selected from: (a) alkyl chains as have been previously defined, (b) wherein R and R' form together an alkylenic chain —$(CH_2)_m$—, being m an integer selected from 4 to 6, optionally substituted by a $C_1$-$C_3$ alkyl group, or (c) wherein R and R' form together a —$(CH_2)_n$—O—$(CH_2)_p$— group, being n and p integers independently selected from 1 to 3. Ether examples are diethyl ether, tert-butylmethyl ether, dioxane, tetrahydrofurane, methyltetrahydrofurane, and mixtures thereof, among others.

As used herein, the term ketone refers to compounds of formula R—C(=O)—R', wherein R and R' are independently selected from an alkyl radical, as has been previously defined. Examples of ketones are acetone and methylisobutylketone and mixtures thereof, among others.

As used herein, the term ester refers to a R—COOR' group, wherein R and R' are independently an alkyl radical, as been previously defined. Examples of esters are ethyl acetate and isobutyl acetate and mixtures thereof.

As used herein, the term gentisic acid is used in the present document to designate the compound whose IUPAC name is 2,5-dihydroxybenzoic acid.

As used herein, the term urea is used in the present document to designate the compound whose formula is $(NH_2)_2$—C=O.

As used herein, the term nicotinamide is used in the present document to designate the compound whose IUPAC name is 3-pyridinecarboxamide.

According to one embodiment of the present invention, the liquid of step a) is selected from the group consisting of water, methanol, ethanol, isopropanol, propanol, butanol, acetonitrile, ethyl acetate, i-butyl acetate, propan-2-one (acetone), methyl-isobutyl-ketone (MIBK), tetrahydrofurane (THF), 1,4-dioxane, dichloromethane (DCM), p-xylene diethylether, methyl tert-butyl ether (TMBE) and heptane, and mixtures of thereof.

The volume of liquid to be used in the process can be determined by the skilled person. Preferably a volume (in ml) between 1-50 times the amount of moles of (1R,3S)-3-(5-cyano-4-phenyl-1,3-thiazol-2-ylcarbamoyl) cyclopentane carboxylic acid is used, more preferably between 1-10 times.

The skilled person can determine, through rutinary procedures, when (1R,3S)-3-(5-cyano-4-phenyl-1,3-thiazol-2-ylcarbamoyl) cyclopentane carboxylic acid cocrystal has been formed, for example using thin layer chromatography, nuclear magnetic resonance or high-performance liquid chromatography.

Once said cocrystal is formed, step b) is carried out, ie, isolating the resulting cocrystal through usual processes in the field of the invention, for example, by filtration.

Preferably, step b) may further comprise steps of washing the resulting cocrystal in order to remove impurities and drying said cocrystal. The washing is preferably carried out with the same liquid as used in step a). The drying is preferably carried out under vacuum and at room temperature.

Combinations and Pharmaceutical Compositions

The invention further provides a combination product comprising the cocrystal of the invention and one or more therapeutic agents selected from: a) angiotensin converting enzyme inhibitors (ACE-inhibitors), b) angiotensin receptor antagonists, c) statins, d) beta blockers, e) calcium antagonists and f) diuretics.

Examples of ACE-inhibitors are, for example, captopril, enalapril, and benazepril, among others.

Examples of antagonists of angiotensin receptor are, for example losartan, azilsartan, irbesartan, and eprosartan, among others.

Examples of statins are, for example, atorvastatin, fluvastatin, simvastatin, and lovastatin, among others.

Examples of beta-blockers are, for example, acebutol, atenolol, betaxolol, carvedilol, and propanolol, among others.

Examples of calcium antagonists are, for example, amlodipine, verapamil, vidipine, and isradipine, among others.

Examples of diuretics are, for example, chlorothiazide, chlorthalidone, furosemide, and spironolactone, among others.

Said combination product may be a pharmaceutical composition comprising the cocrystal and the one or more therapeutic agents. Alternatively, in the combination product the cocrystal and the one or more therapeutic agents are in different compositions.

Moreover, the invention also encompasses pharmaceutical compositions comprising the cocrystal as defined above or a combination as defined above and a pharmaceutically acceptable excipient. In particular, cocrystal is in a therapeutically effective amount. The therapeutic agent, when present, is also preferably in a therapeutically effective amount.

An "effective amount" or "therapeutically effective amount" of a drug or pharmacologically active agent means a non-toxic but sufficient amount of the drug or agent to provide the desired effect. The amount that is "effective" will vary from subject to subject, depending on the age and general condition of the individual, the particular active agent or agents, and the like. Therefore, it is not always possible to specify an exact "effective quantity". However, an appropriate "effective" amount in any individual case can be determined by the skilled person using routine experimentation.

The cocrystal of the present invention and one or more therapeutic agents defined above may be administered simultaneously, sequentially or separately.

Simultaneous administration may, for example, take place in form of a composition comprising the cocrystal of the present invention and one or more therapeutic agents defined above, or by simultaneous administration, ie administration at the same time, of the cocrystal of the present invention and the one or more therapeutic agents defined above that are formulated independently, ie, when they are not part of the same composition.

Sequential administration preferably means administering the cocrystal of the present invention, at a time point, and the one or more therapeutic agents defined above at a different time point, in a staggered manner.

Separate administration preferably means administration of the cocrystal of the present invention and the one or more therapeutic agents defined above, independently of each other at different time points.

The term "pharmaceutically acceptable excipient" refers to a carrier, diluent, or adjuvant which is administered with the active ingredient. Such pharmaceutical excipients may be sterile liquids, such as water and oils, including those of petroleum, animal, vegetable, or synthetic origin, such as peanut oil, soybean oil, mineral oil, sesame oil, and the like. Water or aqueous cocrystal solutions and aqueous solutions of dextrose and glycerol, particularly for injectable solutions, are preferably used as carriers.

Examples of pharmaceutically acceptable excipients for the oral dosage pharmaceutical compositions of the invention are conventional excipients known in the art such as binding agents, for example, syrup, gum arabic, gelatin, sorbitol, tragacanth or polyvinylpyrrolidone; fillers, for example, lactose, mannitol, xylitol, sorbitol, sucrose, corn starch, calcium phosphate, sorbitol, glycine, dextrose, maltodextrin, dextran, dextrin, modified starches; glidants and tablet lubricants, for example magnesium stearate, calcium stearate, stearic acid, zinc stearate, glyceryl monostearate, glyceryl palmitostearate, hydrogenated castor oil, colloidal silicon dioxide, silicon dioxide, anhydrous colloidal silicon, glycerine, hydrogenated vegetable oil, mineral oil, polyethylene glycol, sodium benzoate, sodium lauryl sulfate, sodium stearyl fumarate or talc; disintegrants, for example, starch, polyvinylpyrrolidone, starch sodium glycolate, crospovidone, microcrystalline cellulose, hydroxypropyl cellulose or sorbitan fatty acid esters; pharmaceutically acceptable wetting agents such as sodium lauryl sulfate; water solubilizing aids such as urea, betaine monohydrate, potassium sulfate, potassium acetate, mannitol; alkalinizing agents such as potassium carbonate, sodium carbonate, sodium bicarbonate, trisodium phosphate, tripotassium phosphate, trisodium citrate, tripotassium citrate; sweeteners such as saccharin sodium, sodium cyclamate and aspartame; flavoring agents such as menthol and peppermint oil.

Pharmaceutical compositions of the invention may be administered parenterally, orally or topically, preferably by oral route.

In a preferred embodiment, pharmaceutical compositions are in a dosage form suitable for parenteral administration, such as sterile solutions, suspensions or lyophilized products in the form of a suitable dosage unit. Suitable excipients such as fillers, buffering agents or surfactants may be used.

Pharmaceutical compositions may also be in oral form, either solid or liquid. Suitable dosage forms for oral administration may be tablets, capsules, syrups or powder solutions for solution or oral suspension, granules, sachets. Preferably the dosage form is selected from the group consisting of tablets and capsules.

The above formulations will be prepared using standard methods such as those described or contemplated in the Spanish and US pharmacopoeias and similar reference texts.

Medical Uses

Cocrystals object of the present invention exhibit/maintain a potent antagonist activity on the $A_1$ adenosine receptor.

Thus, the invention is also directed to the use of the cocrystal as described above, a combination product of the cocrystal of the invention together with one or more therapeutic agents as defined above or a pharmaceutical composition such as has been defined above, for use as a medicament.

This aspect may also be formulated as the cocrystal of the invention as described above, a combination product of the cocrystal of the invention together with one or more therapeutic agents as defined above or a pharmaceutical composition as defined above, to prepare a medicament.

Another aspect of the invention is addressed to the cocrystal of the invention as described above, a combination product of the cocrystal of the invention together with one or more therapeutic agents as defined above or a pharmaceutical composition such as has been defined above for use in the treatment and/or prevention of a disease known to ameliorate by $A_1$ adenosine receptor antagonism.

This aspect may also be formulated as the use of the cocrystal of the invention as described above, a combination product of the cocrystal of the invention together with one or more therapeutic agents as defined above or a pharmaceutical composition as defined previously, in the manufacture of a medicament for the treatment and/or prevention of a disease known to ameliorate by $A_1$ adenosine receptor antagonism.

This aspect may also be formulated as a method of treating and/or preventing a disease known to ameliorate by adenosine $A_1$ receptor antagonism, comprising administering to a subject in need of such treatment the cocrystal of the invention as described above, a combination product of the cocrystal of the invention together with one or more therapeutic agents as defined above or a pharmaceutical composition as defined above.

The disease or condition amenable to ameliorate by adenosine $A_1$ receptor antagonism is selected from hypertension, heart failure, ischemia, supraventricular arrhythmia, acute renal failure or any other disease caused by fluid retention, myocardial reperfusion injury, asthma, allergic reactions including but not limited to hypertension, heart failure, ischemia, supraventricular arrhythmia, acute renal failure, myocardial reperfusion injury, asthma, allergic reactions including rhinitis and urticaria, scleroderma and autoimmune diseases, such as multiple sclerosis. In a preferred embodiment, the disease or condition amenable to amelioration by $A_1$ adenosine receptor antagonism is selected from the group consisting of heart failure, acute renal failure, asthma, arterial hypertension, and intradialytic hypotension.

The terms "treat" and "treatment", as used herein, mean reversing, alleviating, inhibiting progression of the disease or condition to which said term or one or more symptoms of said disease or condition applies.

The terms "prevent" and "prevention," as used herein, mean the inhibition of the occurrence of the disease or condition to which this term applies or one or more symptoms of such disease or condition.

In use according to the invention, the cocrystal of the invention, the combination product or the pharmaceutical composition may be administered 1, 2, 3, 4 or 5 times/day. In use, the cocrystal of the invention, the combination product or the pharmaceutical composition may be administered until the symptoms of the disease or conditions to be treated are reversed, alleviated, or inhibited in their progress.

The following non-limiting examples are intended to illustrate the present invention and should not be considered as limitations of the scope of the same.

EXAMPLES

General $^1$H-NMR analysis. Nuclear magnetic resonance analyses were recorded in DMSO-$d_6$ in a Varian Mercury 400 MHz spectrometer, equipped with a broadband probe ATB 1H/19F/X of 5 mm. Spectra were acquired dissolving 5-10 mg of sample in 0.7 mL of deuterated solvent.

XRPD analyses. Diffraction measurements of the starting material and the samples from the screening were performed at ambient conditions on a PANalytical X'Pert PRO θ-θ diffractometer of 240 mm of radius in reflection geometry, equipped with Cu Kα radiation and a PIXcel detector, operated at 45 kV and 40 mA. Each sample was mounted on a zero-background silicon holder and allowed to spin at 0.25 rev/s during the data collection. The measurement angular range was 3.0-40.0° (2θ) with a step size of 0.013°. The scanning speed was 0.082°/s (40.80 s/step) for starting materials and 0.328°/s (10.20 s/step) for the samples generated during the study.

DSC analyses were recorded with a Mettler Toledo DSC2. The sample was weighed into a 40 μl aluminium crucible with a pinhole lid and heated from 25 to 300° C. at a rate of 10° C./min, under nitrogen (50 ml/min).

Crystalline stability study was performed under accelerated stability conditions (40° C., 75±5 RH %) for one week. A sample of each form stored on a XRPD silicon holder was exposed in a climatic chamber. It is worth noting that these conditions are very drastic because the high surface exposed to the storage conditions might favour possible crystalline conversion. The samples were periodically analysed by XRPD to observe possible transformation.

Additional crystalline stability study was performed under accelerated stability conditions (40° C., 75±5 RH %). Cocrystal samples were stored in an open vial and exposed in a climate chamber maintaining the conditions set with accuracy (40° C.-75% RH ±5 RH). These samples were analysed weekly for 1 month.

Hygroscopicity study. The hygroscopicity of cocrystals was determined by DVS (Dynamic Vapour Sorption) with a Q5000 TA instrument. This is a gravimetric technique that measures the amount of water absorbed or desorbed by a sample at different relative humidities (RH). At each RH level, the sample mass must be allowed to reach gravimetric equilibrium (or surpass the time limit) before progressing to the next humidity level. Sorption and desorption isotherms were performed at 25° C. over a range of 0-95% RH. The sample was not previously dried, but it was exposed to 0% RH until reaching a stable weight before starting the DVS cycle. This equilibration step allows the elimination of the possible adsorbed humidity from the atmosphere. The relative humidity (RH) was controlled by a mixture of wet and dry nitrogen stream. The RH was held constant until the equilibrium had been obtained (constant weight) or until the maximum time has been reached, before changing the RH to the next level.

Example 1. Synthesis of (1R,3S)-3-(5-Cyano-4-Phenyl-1,3-Thiazol-2-Ylcarbamoyl)Cyclopentane Carboxylic Acid The synthesis of compound (1R,3S)-3-(5-cyano-4-phenyl-1,3-thiazol-2-ylcarbamoyl) cyclopentane carboxylic acid is described in detail in patent application WO 2009/044250 A1, which is incorporated herein by reference.

$^1$H-NMR (300 MHz, DMSO-$d_6$): δ=1.88 (m, 4H), 1.99 (m, 1H), 2.22 (m, 1H), 2.79 (m, 1H), 3.06 (m, 1H), 7.57 (m, 3H), 7.99 (m, 2H), 12.37 (s, 1H), 12.89 (s, 1H).

FIG. 1 illustrates the $^1$H NMR spectrum of (1R,3S)-3-(5-cyano-4-phenyl-1,3-thiazol-2-ylcarbamoyl) cyclopentane carboxylic acid.

Figure 2:
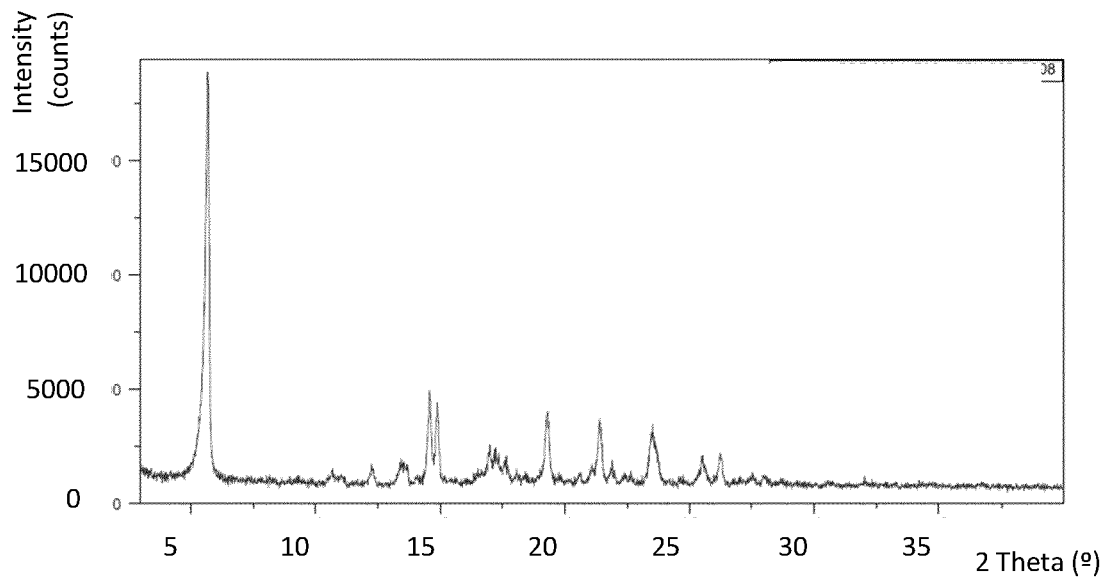
FIG. 2 illustrates XRPD pattern of (1R,3S)-3-(5-cyano-4-phenyl-1,3-thiazol-2-ylcarbamoyl) cyclopentane carboxylic acid.

FIG. 2 illustrates the XRPD pattern of (1R,3S)-3-(5-cyano-4-phenyl-1,3-thiazol-2-ylcarbamoyl) cyclopentane carboxylic acid.

Figure 3:
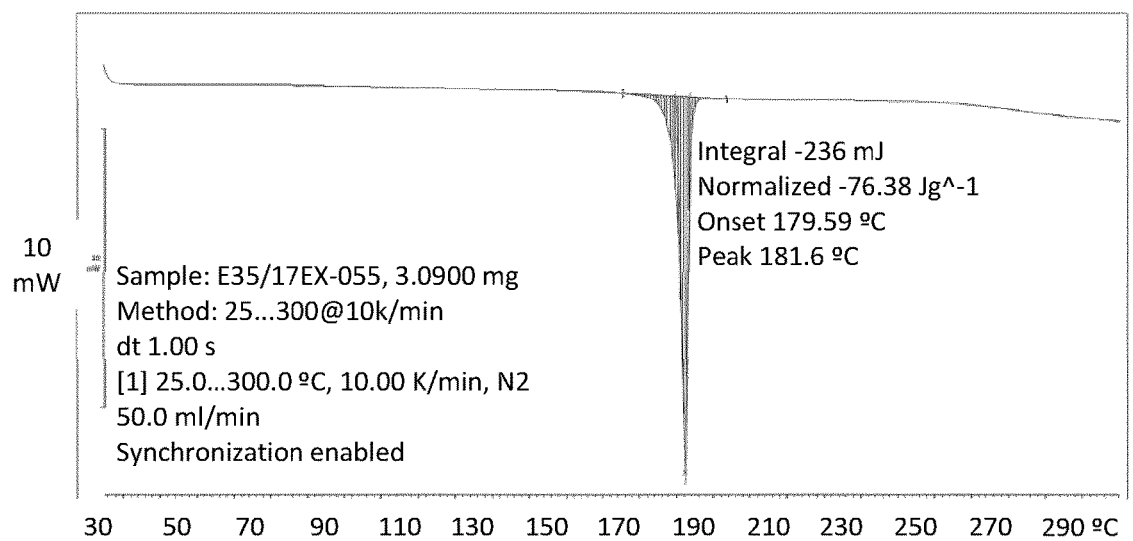
FIG. 3 illustrates DSC pattern of (1R,3S)-3-(5-cyano-4-phenyl-1,3-thiazol-2-ylcarbamoyl) cyclopentane carboxylic acid, showing an endothermic event with an onset at 179.59° C. which correspond to the melting point of this compound.

FIG. 3 illustrates the DSC pattern of (1R,3S)-3-(5-cyano-4-phenyl-1,3-thiazol-2-ylcarbamoyl) cyclopentane carboxylic acid, showing an endothermic event with an onset at 179.59° C. which correspond to the melting point of this compound.

Example 2. Preparation of the Cocrystal of (1R, 3S)-3-(5-Cyano-4-Phenyl-1,3-Thiazol-2-Ylcarbamoyl)Cyclopentane Carboxylic Acid and Gentisic Acid To a round bottomed flask, equipped with magnetic stirrer and containing a mixture of (1R,3S)-3-(5-cyano-4-phenyl-1,3-thiazol-2-ylcarbamoyl) cyclopentane carboxylic acid (300 mg, 0.88 mmol) and gentisic acid (169 mg, 1.10 mmol, 1.25 eq.), TBME (3 ml) was added. The resulting mixture was stirred at room temperature for 15 hours. Then, the suspension was filtered through a sinter funnel (porosity n° 3) and washed with TBME (2×0.2 mL). After drying under vacuum at RT, the cocrystal of (1R,3S)-3-(5-cyano phenyl-1,3-thiazol-2-ylcarbamoyl) cyclopentane carboxylic acid and gentisic acid was obtained as a white solid.

Figure 4:
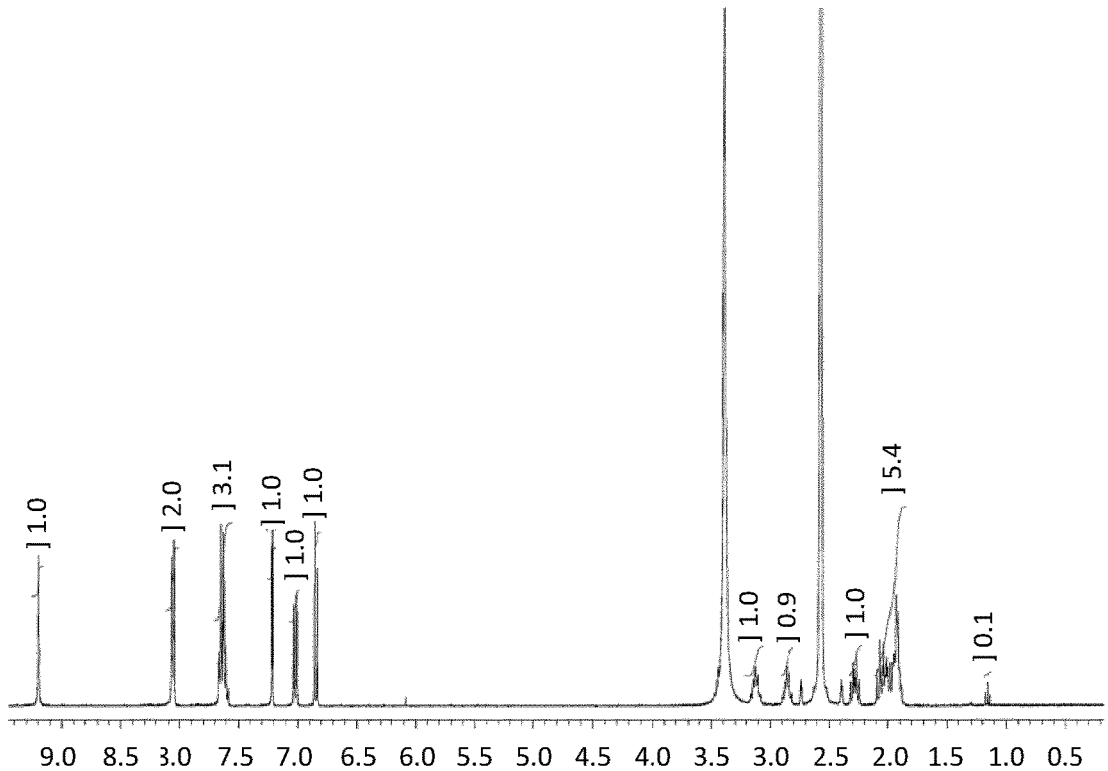
FIG. 4 illustrates $^1$H NMR spectrum of the cocrystal of (1R,3S)-3-(5-cyano-4-phenyl-1,3-thiazol-2-ylcarbamoyl) cyclopentane carboxylic acid and gentisic acid of example 2.

FIG. 4 illustrates 1H-NMR pattern spectrum of the cocrystal of (1R,3S)-3-(5-cyano phenyl-1,3-thiazol-2-ylcarbamoyl) cyclopentane carboxylic acid and gentisic acid of example 2, confirming a 1:1 molar ratio.

Figure 5:
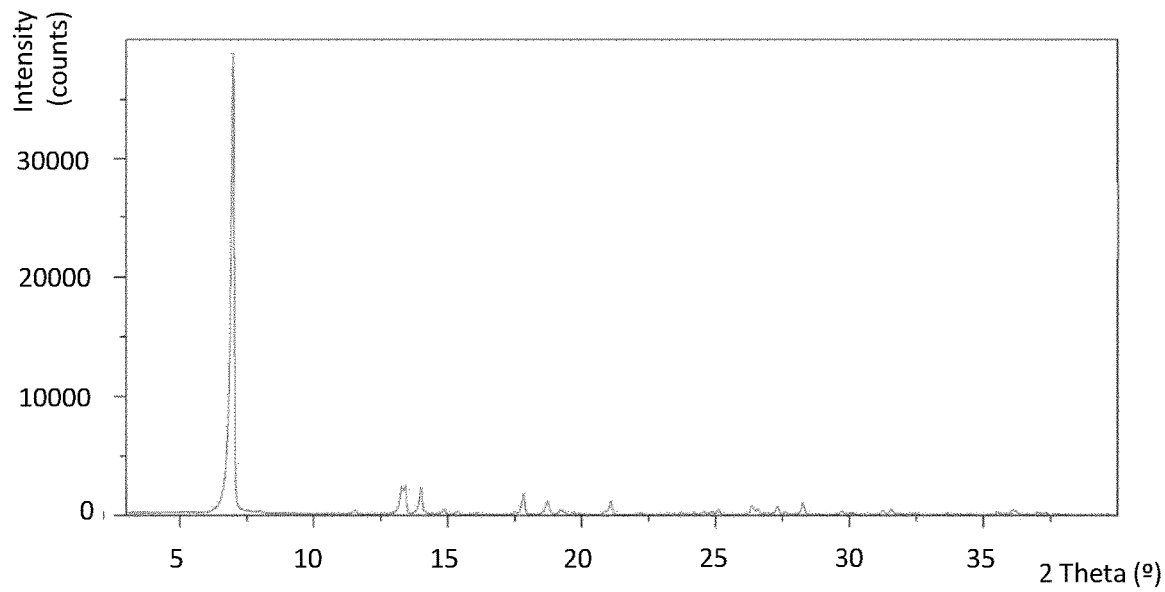
FIG. 5 illustrates XRPD pattern of the cocrystal of (1R, 3S)-3-(5-cyano-4-phenyl-1,3-thiazol-2-ylcarbamoyl) cyclopentane carboxylic acid and gentisic acid of example 2.

The cocrystal of example 2 is also characterized by a XRPD. FIG. 5 shows the corresponding pattern and Table 2 shows main peaks.

TABLE 2

| Pos. [°2Th ± 0.2] | Relative Intensity [%] |
|---|---|
| 6.99 | 100 |
| 13.29 | 6.2 |
| 13.42 | 6.3 |
| 14.02 | 5.6 |
| 17.82 | 4.2 |
| 18.71 | 2.7 |
| 21.09 | 3 |
| 26.34 | 1.8 |
| 26.58 | 1.1 |
| 27.28 | 1.5 |
| 28.24 | 2.5 |
| 31.56 | 1.1 |

Figure 6:
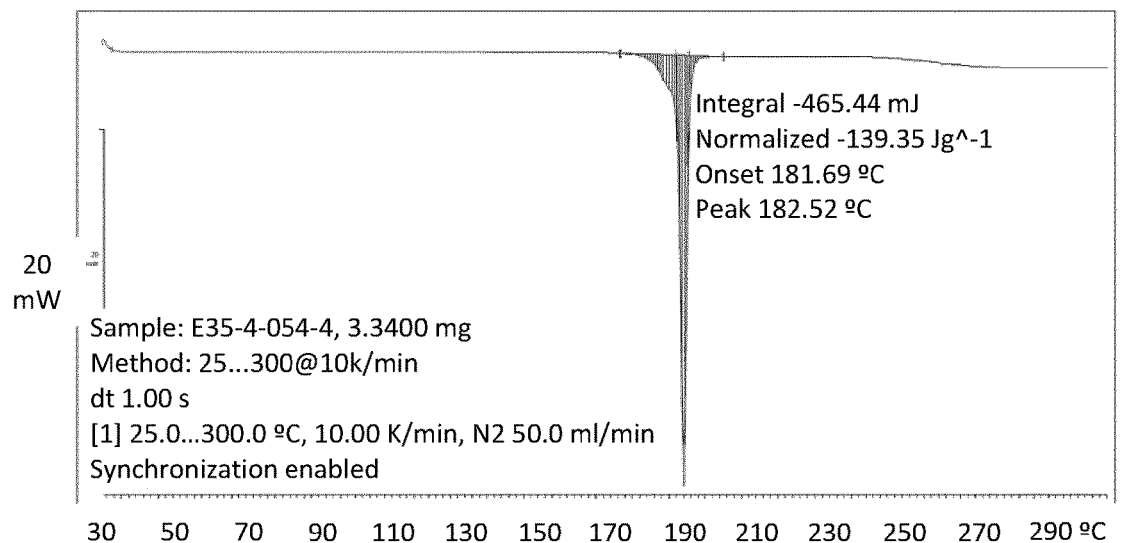
FIG. 6 illustrates DSC pattern of the cocrystal of (1R, 3S)-3-(5-cyano-4-phenyl-1,3-thiazol-2-ylcarbamoyl) cyclopentane carboxylic acid and gentisic acid of example 2, showing an endothermic event with an onset at 181.69° C. which correspond to the melting point of this cocrystal.

FIG. 6 illustrates DSC pattern of the cocrystal of example 2, showing an endothermic event with an onset at 181.69° C. which correspond to the melting point of said cocrystal.

Example 3. Preparation of the Cocrystal of (1R, 3S)-3-(5-Cyano-4-Phenyl-1,3-Thiazol-2-Ylcarbamoyl)Cyclopentane Carboxylic Acid and Urea Cocrystal To a round bottomed flask, equipped with magnetic stirrer and containing a mixture of (1R,3S)-3-(5-cyano-4-phenyl-1,3-thiazol-2-ylcarbamoyl) cyclopentane carboxylic acid (260 mg, 0.77 mmol, 1.3 eq.) and urea (35.2 mg, 0.59 mmol), ACN (2 mL) was added. The resulting mixture was stirred at RT temperature for 15 hours. Then, the suspension was filtered through a sinter funnel (porosity n° 3) and washed with ACN (2×0.2 mL). After drying under vacuum at RT, a cocrystal of (1R,3S)-3-(5-cyano-4-phenyl-1,3-thiazol-2-ylcarbamoyl) cyclopentane carboxylic acid and urea was obtained as a white solid.

Figure 7:
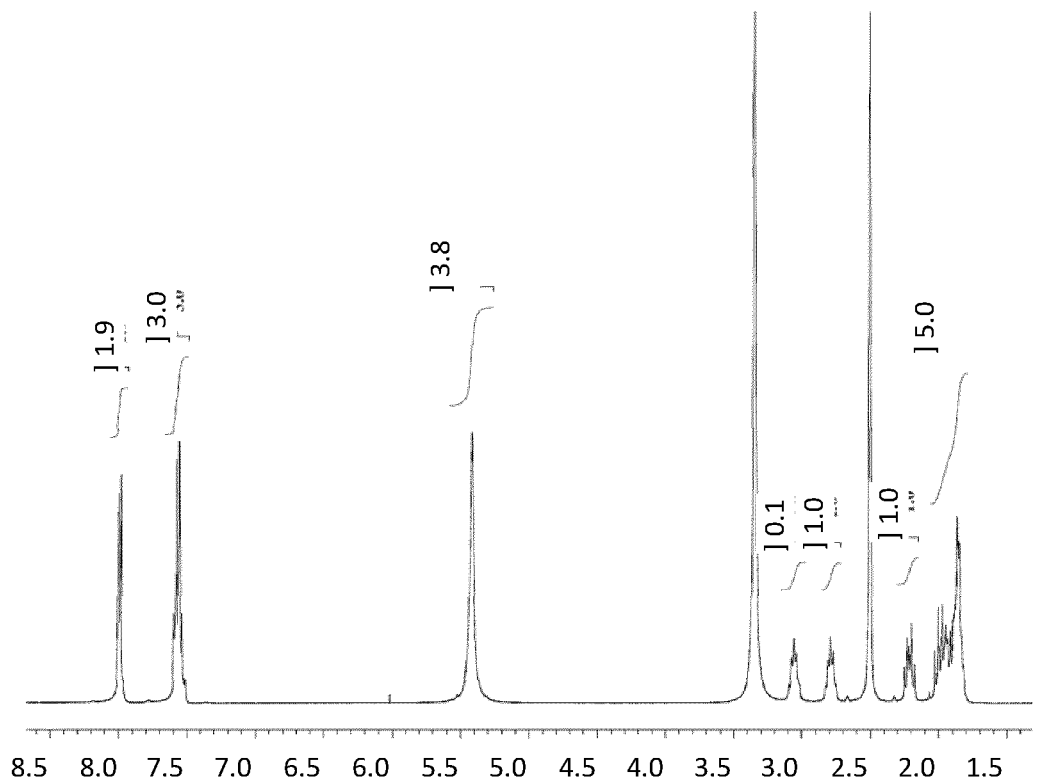
FIG. 7 illustrates $^1$H NMR spectrum of the cocrystal of (1R,3S)-3-(5-cyano-4-phenyl-1,3-thiazol-2-ylcarbamoyl) cyclopentane carboxylic acid and urea of example 3.

FIG. 7 illustrates 1H-NMR pattern spectrum of the cocrystal of (1R,3S)-3-(5-cyano phenyl-1,3-thiazol-2-ylcarbamoyl) cyclopentane carboxylic acid and urea, confirming a 1:1 molar ratio.

Figure 8:
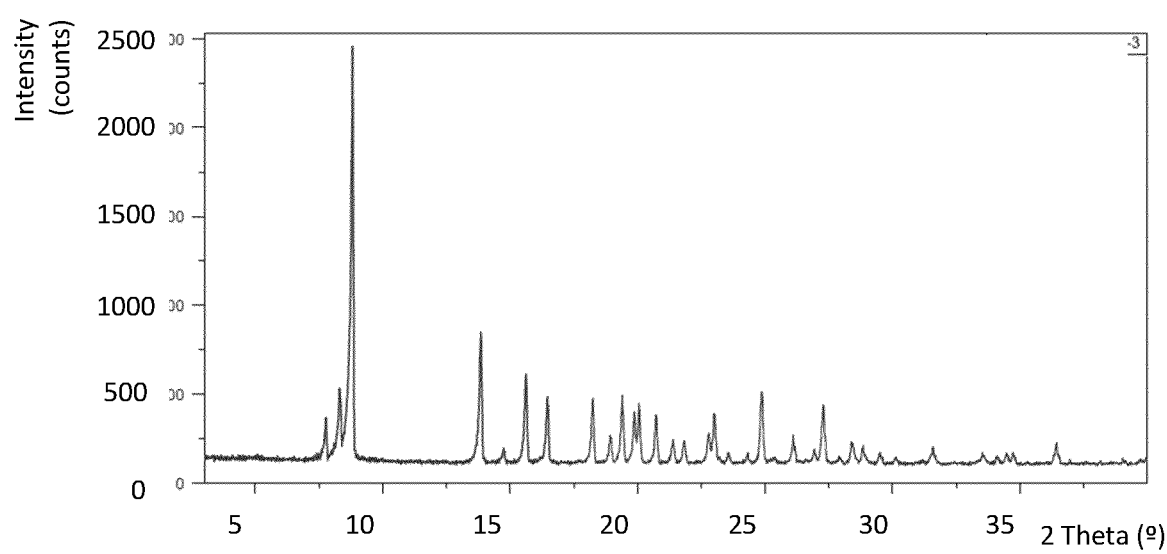
FIG. 8 illustrates XRPD pattern of the cocrystal of (1R, 3S)-3-(5-cyano-4-phenyl-1,3-thiazol-2-ylcarbamoyl) cyclopentane carboxylic acid and urea of example 3.

The cocrystal of example 3 is also characterized by a XRPD. FIG. 8 shows the corresponding pattern and Table 3 shows main peaks.

TABLE 3

| Pos. [°2Th ± 0.2] | Relative Intensity [%] |
|---|---|
| 7.77 | 7 |
| 8.32 | 27 |
| 8.82 | 100 |
| 13.86 | 31 |
| 15.60 | 19 |
| 16.47 | 18 |
| 18.23 | 17 |
| 18.94 | 6 |
| 19.38 | 14 |

TABLE 3-continued

| Pos. [°2Th ± 0.2] | Relative Intensity [%] |
|---|---|
| 19.86 | 16 |
| 20.05 | 15 |
| 20.71 | 10 |
| 21.38 | 7 |
| 21.84 | 5 |
| 22.76 | 7 |
| 23.02 | 11 |
| 24.86 | 19 |
| 26.10 | 6 |
| 27.28 | 16 |
| 28.40 | 6 |

Figure 9:
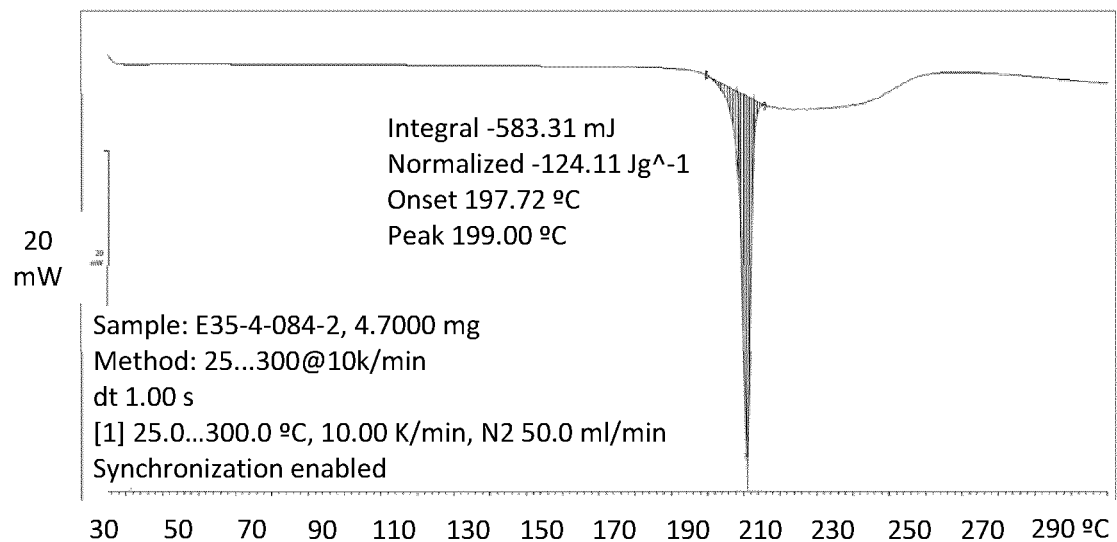
FIG. 9 illustrates DSC pattern of the cocrystal of (1R, 3S)-3-(5-cyano-4-phenyl-1,3-thiazol-2-ylcarbamoyl) cyclopentane carboxylic acid and urea cocrystal of example 3, showing an endothermic event with an onset at 197.7° C. which correspond to the melting point of this cocrystal.

FIG. 9 illustrates DSC pattern of the cocrystal of example 3, showing an endothermic event with an onset at 197.72° C. which correspond to the melting point of this cocrystal.

Example 4. Preparation of the Cocrystal of (1R, 3S)-3-(5-Cyano-4-Phenyl-1,3-Thiazol-2-Ylcarbamoyl)Cyclopentane Carboxylic Acid and Nicotinamide Cocrystal To a round flask equipped with magnetic stirrer, containing a mixture of (1R,3S)-3-(5-cyano-4-phenyl-1,3-thiazol-2-ylcarbamoyl) cyclopentane carboxylic acid (400 mg, 1.17 mmol, 2 eq.) and nicotinamide (71.5 mg, 0.59 mmol), was added MIBK (4 mL). The resulting mixture was stirred at room temperature for 15 hours. Then, the suspension was filtered through a sinter funnel (porosity n° 3) and washed with MIBK (3×0.2 mL). After drying under vacuum at RT, a cocrystal of (1R,3S)-3-(5-cyano-4-phenyl-1,3-thiazol-2-ylcarbamoyl) cyclopentane carboxylic acid and nicotinamide was obtained as a white solid.

Figure 10:
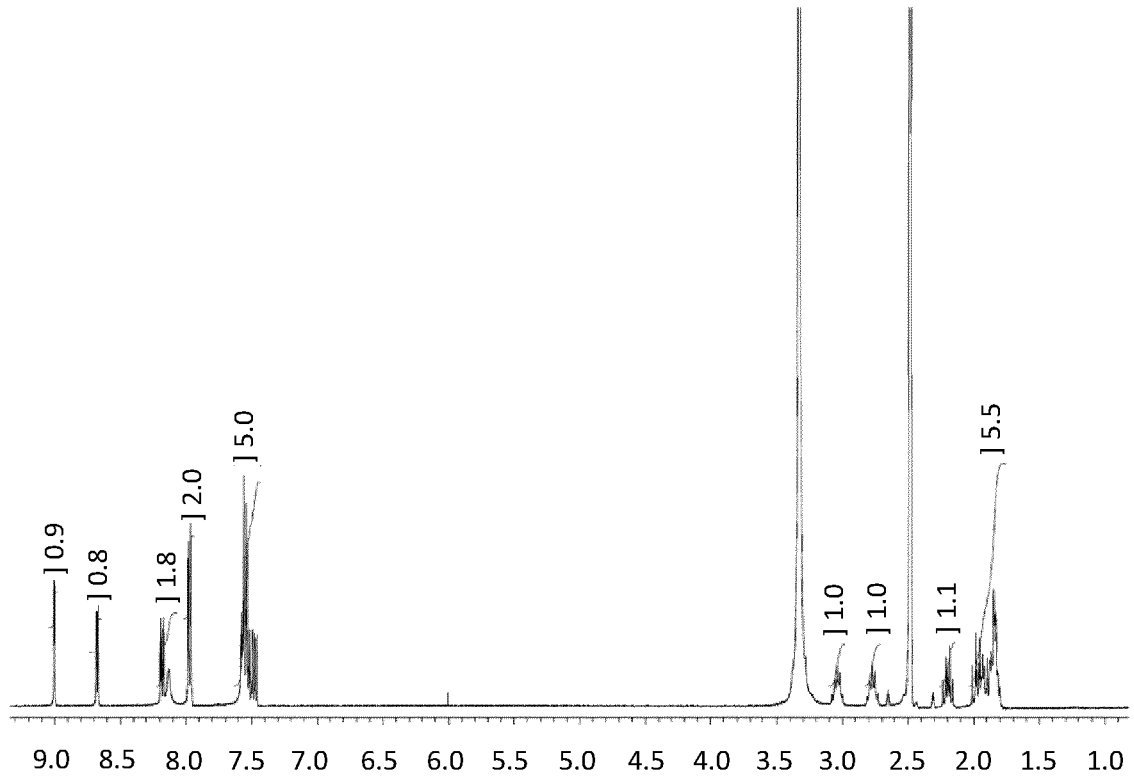
FIG. 10 illustrates $^1$H NMR spectrum of the cocrystal of (1R,3S)-3-(5-cyano-4-phenyl-1,3-thiazol-2-ylcarbamoyl) cyclopentane carboxylic acid and nicotinamide of example 4.

FIG. 10 illustrates $^1$H-NMR pattern spectrum of the cocrystal of (1R,3S)-3-(5-cyano-4-phenyl-1,3-thiazol-2-ylcarbamoyl) cyclopentane carboxylic acid and nicotinamide, confirming the 1:1 molar ratio.

Figure 11:
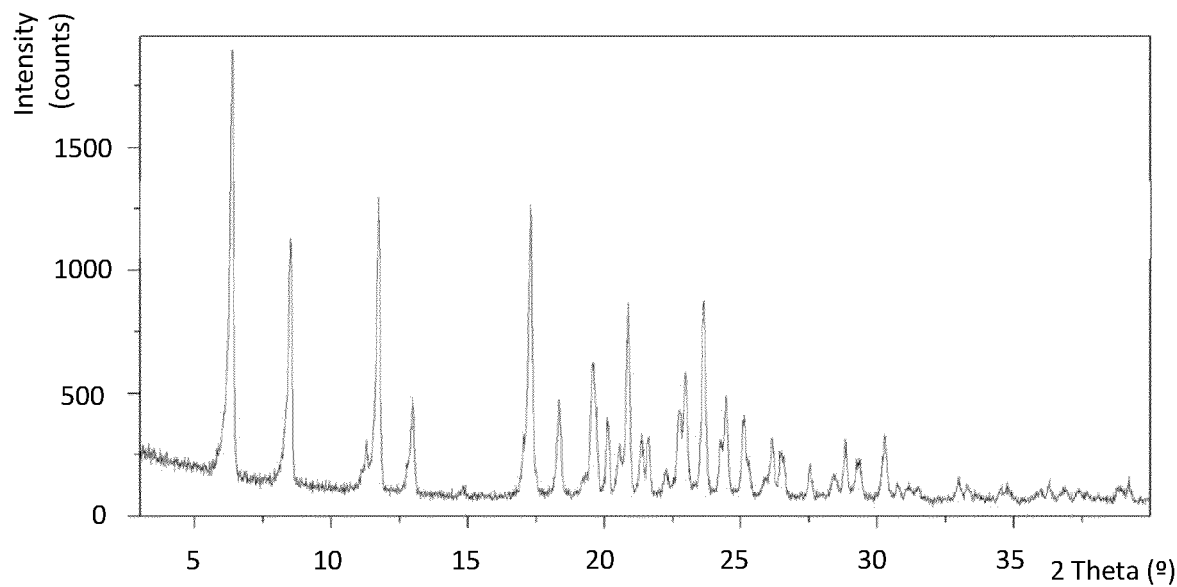
FIG. 11 illustrates XRPD pattern of the cocrystal of (1R,3S)-3-(5-cyano-4-phenyl-1,3-thiazol-2-ylcarbamoyl) cyclopentane carboxylic acid and nicotinamide of example 4.

The cocrystal of example 4 is also characterized by a XRPD. FIG. 11 shows the corresponding pattern and Table 4 shows main peaks.

TABLE 4

| Pos. [°2Th ± 0.2] | Relative Intensity [%] |
|---|---|
| 6.40 | 100 |
| 8.54 | 55 |
| 11.28 | 11 |
| 11.75 | 64 |
| 13.02 | 20 |
| 17.29 | 70 |
| 18.33 | 24 |
| 19.56 | 32 |
| 20.11 | 15 |
| 20.55 | 11 |
| 20.88 | 41 |
| 21.36 | 12 |
| 21.62 | 13 |
| 22.73 | 19 |
| 22.96 | 29 |
| 23.66 | 44 |
| 24.26 | 12 |
| 24.46 | 23 |

TABLE 4-continued

| Pos. [°2Th ± 0.2] | Relative Intensity [%] |
|---|---|
| 25.12 | 19 |
| 26.17 | 13 |
| 26.46 | 11 |
| 27.53 | 7 |
| 28.81 | 12 |
| 29.36 | 8 |
| 30.28 | 15 |
| 32.96 | 5 |

Figure 12:
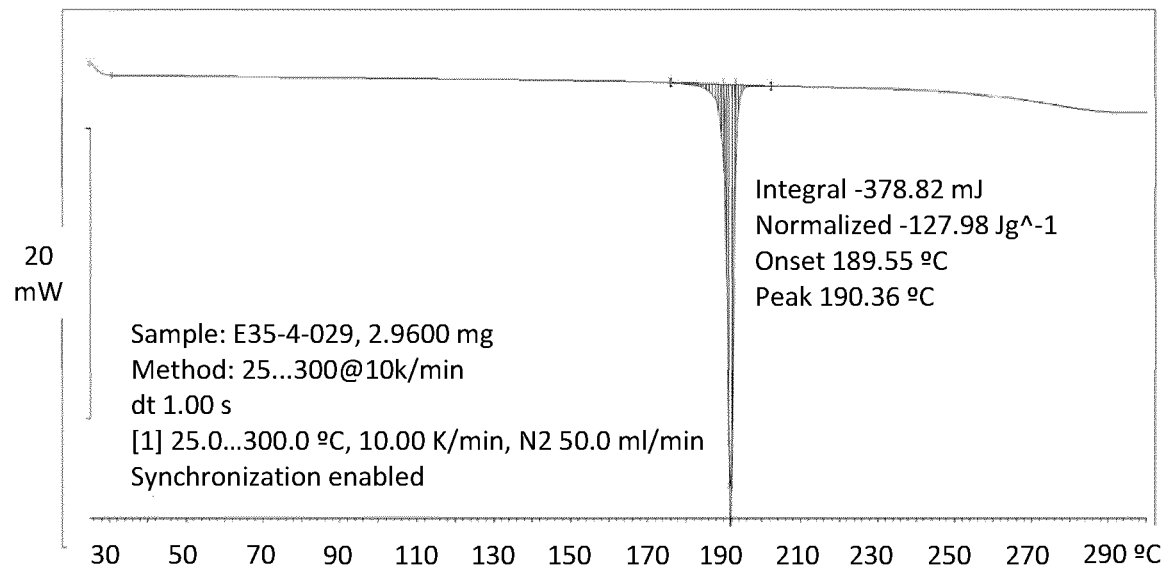
FIG. 12 illustrates DSC pattern of the cocrystal of (1R, 3S)-3-(5-cyano-4-phenyl-1,3-thiazol-2-ylcarbamoyl) cyclopentane carboxylic acid and nicotinamide of example 4, showing an endothermic event with an onset at 189.55° C. which correspond to the melting point of this cocrystal.
Figure 13:
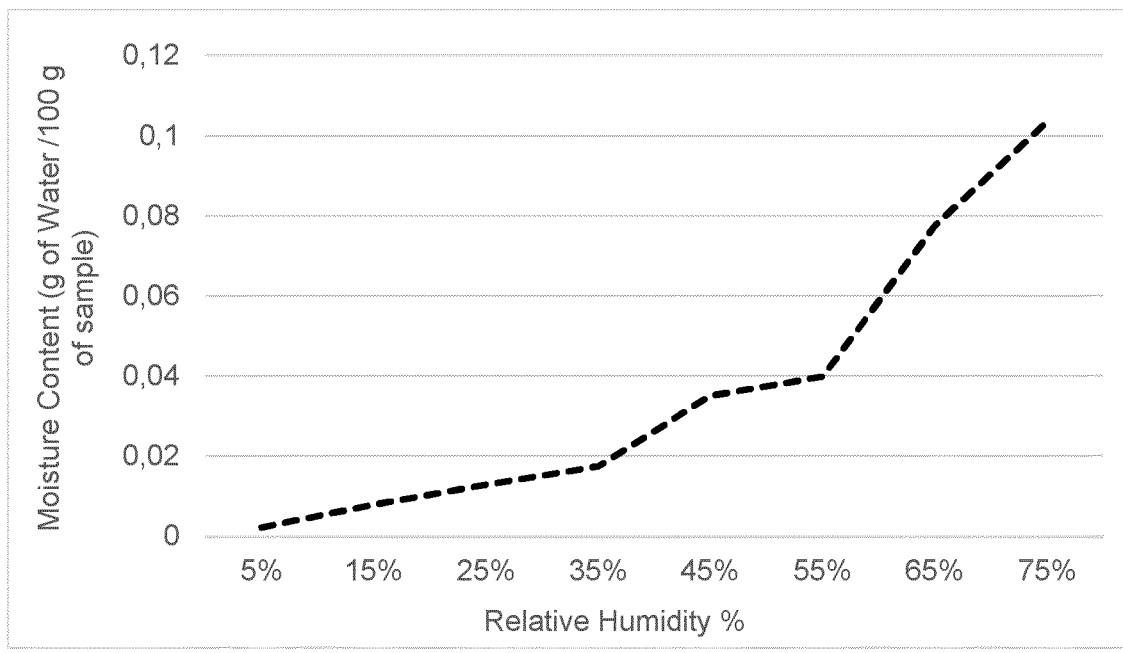
FIG. 13 illustrates DVS pattern of the cocrystal of (1R, 3S)-3-(5-cyano-4-phenyl-1,3-thiazol-2-ylcarbamoyl) cyclopentane carboxylic acid and gentisic acid of example 2, showing the change in weight (in %) of said cocrystal as a function of relative humidity (RH).
Figure 14:
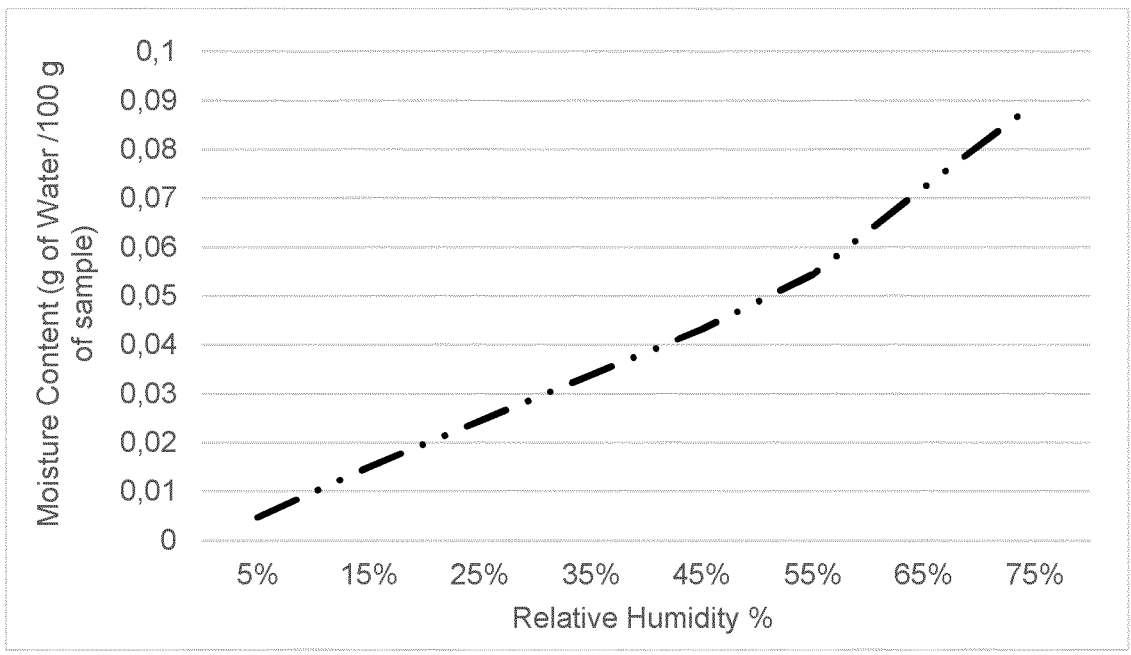
FIG. 14 illustrates DVS pattern of the cocrystal of (1R, 3S)-3-(5-cyano-4-phenyl-1,3-thiazol-2-ylcarbamoyl) cyclopentane carboxylic acid and urea of example 3, showing the change in weight (in %) of said cocrystal as a function of relative humidity (RH).
Figure 15:
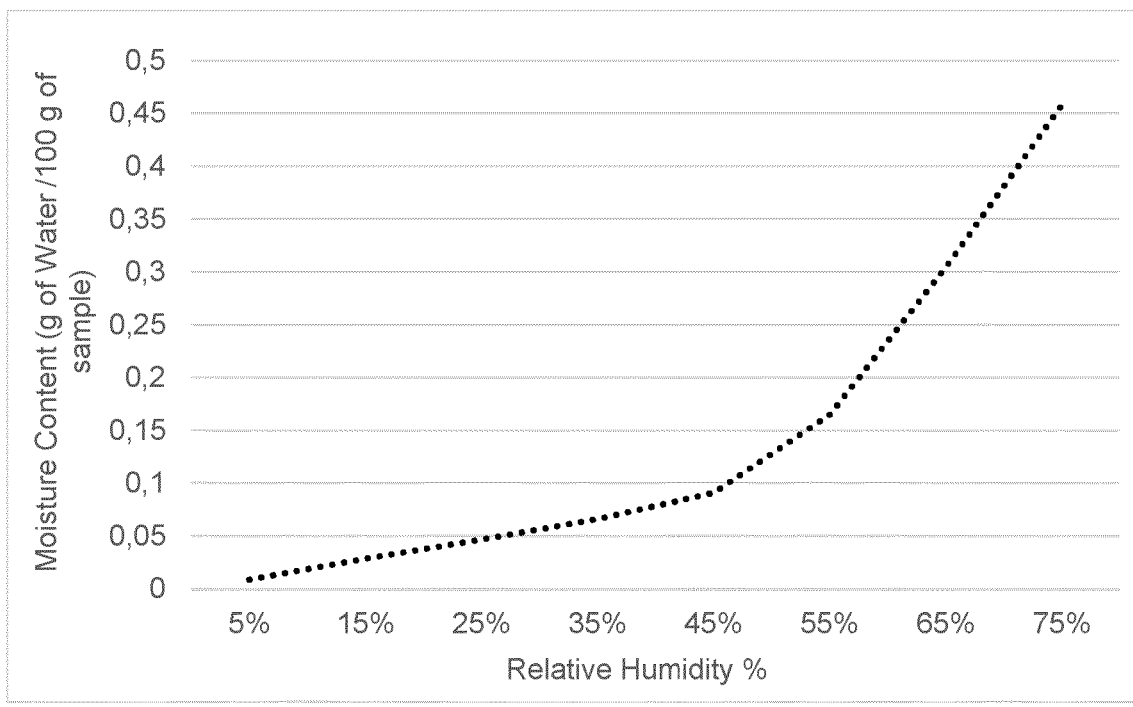
FIG. 15 illustrates DVS pattern of the cocrystal of (1R, 3S)-3-(5-cyano-4-phenyl-1,3-thiazol-2-ylcarbamoyl) cyclopentane carboxylic acid and nicotinamide of example 4, showing the change in weight (in %) of said cocrystal as a function of relative humidity (RH).
Figure 16:
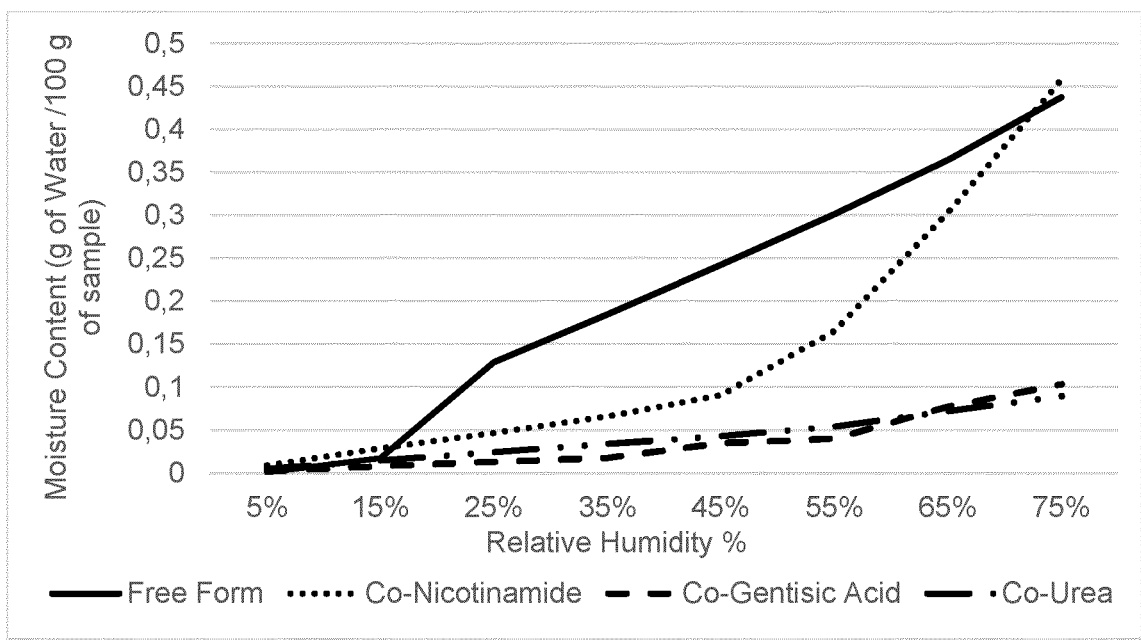
FIG. 16 shows a comparison between the DVS patterns of (1R,3S)-3-(5-cyano phenyl-1,3-thiazol-2-ylcarbamoyl) cyclopentane carboxylic acid and the different cocrystals obtained in examples 2, 3 and 4.

FIG. 12 illustrates DSC pattern of the cocrystal of example 4, showing an endothermic event with an onset at 189.55° C. which correspond to the melting point of this cocrystal.

Example 5. Stability Assay

The stability of the cocrystalline forms of (1R,3S)-3-(5-cyano-4-phenyl-1,3-thiazol ylcarbamoyl) cyclopentane carboxylic acid were studied under accelerated storage conditions (40° C., 75±5 RH %) for one to four week. See results in Table 5.

TABLE 5

| Compound | 1 week | 2 weeks | 3 weeks | 4 weeks |
|---|---|---|---|---|
| Example 2: Cocrystal of (1R,3S)-3-(5-cyano-4-phenyl-1,3-thiazol-2-ylcarbamoyl)cyclopentane carboxylic acid and gentisic acid | stable | stable | stable | stable |
| Example 3: Cocrystal of (1R,3S)-3-(5-cyano-4-phenyl-1,3-thiazol-2-ylcarbamoyl)cyclopentane carboxylic acid and urea | stable | stable | stable | stable |
| Example 4: Cocrystal of (1R,3S)-3-(5-cyano-4-phenyl-1,3-thiazol-2-ylcarbamoyl)cyclopentane carboxylic acid and nicotinamide | stable | stable | stable | stable |

After time exposure, cocrystals remained stable according to XRPD analysis. Amorphization or appearance of crystalline forms was not detected in the limit of detection of the analysis conditions.

Example 6. Hygroscopicity Study

The table below (Table 6) shows the moisture content of parent carboxylic acid and cocrystals in the hygroscopicity study.

TABLE 6

| Compound | 15% RH | 35% RH | 55% RH | 75% RH |
|---|---|---|---|---|
| Example 1: (1R,3S)-3-(5-cyano-4-phenyl-1,3-thiazol-2-ylcarbamoyl)cyclopentane carboxylic acid | 0.0168 | 0.1842 | 0.3008 | 0.4369 |
| Example 2: Cocrystal of (1R,3S)-3-(5-cyano-4-phenyl-1,3-thiazol-2-ylcarbamoyl)cyclopentane carboxylic acid and gentisic acid | 0.0079 | 0.0175 | 0.0398 | 0.1035 |
| Example 3: Cocrystal of (1 R,3S)-3-(5-cyano-4-phenyl-1,3-thiazol-2-ylcarbamoyl)cyclopentane carboxylic acid and urea | 0.015 | 0.0339 | 0.0545 | 0.0895 |
| Example 4: Cocrystal of (1R,3S)-3-(5-cyano-4-phenyl-1,3-thiazol-2-ylcarbamoyl)cyclopentane carboxylic acid and nicotinamide | 0.029 | 0.066 | 0.165 | 0.4584 |

As it can be seen from the above table, the cocrystal with gentisic acid and the cocrystal with urea are less hygroscopic than free acid, specially up to 75% RH. See FIGS. 13-16.

Example 7. Oral Bioavailability Assays

The objective of this study was to investigate the plasma pharmacokinetics of differentes cocrystals obtained from (1R,3S)-3-(5-cyano-4-phenyl-1, 3-thiazol ylcarbamoyl) cyclopentane carboxylic acid, following a single intravenous (IV) and oral (PO) administration in male SD rats.

Animals were divided into two groups: Group 1 (IV: 1 mg/kg) and Group 2 (PO: 5 mg/kg). Animals in Group 1 and 2 were administered a solution of the different cocrystals of (1R,3S)-3-(5-cyano-4-phenyl-1,3-thiazol-2-ylcarbamoyl) cyclopentane carboxylic acid in normal saline. The blood samples were collected from set of three rats at each time point in labeled micro centrifuge tube containing $K_2EDTA$ solution as anticoagulant at Pre-dose, 0.083, 0.25, 0.5, 1, 2, 4, 8 and 24 hr (IV) and Pre-dose, 0.25, 0.5, 1, 2, 4, 6, 8 and 24 hr (PO). Plasma samples were separated by centrifugation of whole blood and stored below −70±10° C. until bioanalysis. All samples were processed for analysis by protein precipitation using acetonitrile and analyzed with fit-for-purpose LC-MS/MS method (LLOQ=1.00 ng/ml). Pharmacokinetic parameters were calculated using the non-compartmental analysis tool of Phoenix WinNonlin® (Version 6.3).

Main pharmacokinetic parameters obtained from Examples 1-4 are shown in Table 7 below.

As it can be seen from the above table, cocrystals with gentisic acid, urea and nicotinamide presents higher bioavailability compared to free acid.

Example 8. Comparative Bioavailability Assay in Healthy Volunteers

Healthy volunteers in this study will be males 18 years of age or older in order to assess the comparative bioavailability of compound of Example 2 versus compound of Example 1, under fasting conditions and to investigate the effect of a high fat, high calorie meal. Compounds will be administered orally in single dose of Example 1 (5 mg) and Example 2 (7.3 mg). The study will have a randomized, open-label, four-fold crossover design.

In order to determine comparative bioavailability $AUC_{0-t}$ ($AUC_{0-t}$: Area under the plasma concentration-time curve from time 0 h to the last measurable concentration) and $C_{max}$ ($C_{max}$: Observed maximum plasma concentration (peak exposure)) will be determined after each administration.

Results 16 volunteers were included in the study. In all of the volunteers, basal samples showed no presence of the compound of Example 1. Therefore, all the data were included in all pharmacokinetic measurements and calculations, without any adjustment. See Table 8.

TABLE 7

| Compound | Route | Dose (mg/Kg) | $C_{max}$ (ng/ml) | $AUC_{last}$ (ng/ml *hr) | Clearance (ml/min/kg) | F % |
|---|---|---|---|---|---|---|
| Example 1: (1R,3S)-3-(5-cyano-4-phenyl-1,3-thiazol-2-ylcarbamoyl)cyclopentane carboxylic acid | iv po | 1 5 | — 2012 | 2204.38 5200.71 | 6.3 — | — 47 |
| Example 2: Cocrystal of (1R,3S)-3-(5-cyano-4-phenyl-1,3-thiazol-2-ylcarbamoyl)cyclopentane carboxylic acid and gentistic acid | iv po | 1 5 | — 8642.28 | 3304.55 16502.48 | 5.03 — | — 100 |
| Example 3: (1R,3S)-3-(5-cyano-4-phenyl-1,3-thiazol-2-ylcarbamoyl)cyclopentane carboxylic acid and urea | iv po | 1 5 | — 10227.47 | 2714.55 19238.03 | 6.12 — | — 100 |
| Example 4: (1R,3S)-3-(5-cyano-4-phenyl-1,3-thiazol-2-ylcarbamoyl)cyclopentane carboxylic acid and nicotinamide | | | | | | | po: oral administration (per os)
iv: intravenous administration
$C_{max}$ refers to the maximum plasma drug concentration obtained after oral administration of a drug between the time of dosing and the final observed time point.
$AUC_{last}$ refers to the area under the curve from the time of dosing to the time of last observation that is greater than the limit of quantitation.
Clearance refers to the measurement of the ability of the body to remove drug from the plasma and iis calculated from the intravenous dosing.
F % refers to the bioavailibility. The systemic availability of a compound after oral administration is calculated using the following equation: F (%) = ($AUC_{last}$ PO × Dose IV/$AUC_{last}$ IV × Dose PO) × 100

TABLE 8

| Metric | Example 1 MEAN ± SD (geometric mean) Fasting | Example 2 MEAN ± SD (geometric mean) Fasting | Example 1 MEAN ± SD (geometric mean) Fed | Example 2 MEAN ± SD (geometric mean) Fed |
|---|---|---|---|---|
| $AUC_{0-t}$ (ng/mL×h) | 1155.0 ± 567.8 (1052.8) | 1138.5 ± 451.1 (1071.4) | 588.1 ± 160.9 (567.9) | 599.1 ± 132.1 (585.9) |
| $AUC_{0-\infty}$ (ng/mL×h) | 1257.2 ± 661.9 (1132.2) | 1216.5 ± 483.3 (1141.7) | 657.9 ± 191.4 (632.7) | 675.0 ± 158.8 (659.1) |
| Cmax (ng/mL) | 186.7 ± 71.6 (175.9) | 173.7 ± 60.7 (165.8) | 68.0 + 18.6 (65.6) | 73.6 ± 25.1 (69.8) |
| tmax (h)* | 2.5 (1.5-4.0) | 2.25 (1.5-5.0) | 7.0 (5.0-7.0) | 7.0 (5.0-7.0) |

*median and range
$AUC_{0-t}$ = Area under the curve of plasma concentrations with respect to time up to the last quantifiable sample (time t), calculated using the trapezoidal method.
$AUC_{0-\infty}$: area under the curve with respect to time, extrapolated to infinity, calculated as follows: $AUC_{0-\infty}$ = $AUC_{0-t}$ + $C_t$/ke, where $C_t$ is the quantified concentration in time t and ke is the elimination constant. The latter will be calculated using a linear regression analysis during the last monoexponential phase of elimination (Phoenix WinNonLin). In all cases at least three plasma concentration values will be used to define that phase.
Cmax: maximum concentration.
tmax = time for reaching $C_{max}$.

The bioavailability of Example 1 was similar to that of Example 2, with the 90% confidence intervals falling within the acceptance limits for bioequivalence (80.00%-125.00%) in the case of $AUC_{0-t}$ and $C_{max}$ under fasting condition and in the case of $AUC_{0-t}$ under fed condition. $C_{max}$ of Example 2 was slightly higher when it was administered after a high fat meal.

The invention claimed is:

1. A cocrystal comprising:
 a) (1R,3S)-3-(5-cyano-4-phenyl-1,3-thiazol-2-ylcarbamoyl) cyclopentane carboxylic acid, and
 b) a cocrystal forming compound selected from the group consisting of gentisic acid, urea and nicotinamide.

2. The cocrystal according to claim 1 wherein the cocrystal forming compound is gentisic acid.

3. The cocrystal according to claim 2 wherein the molar ratio of (1R,3S)-3-(5-cyano-4-phenyl-1,3-thiazol-2-ylcarbamoyl) cyclopentane carboxylic acid to gentisic acid in said cocrystal is comprised between 0.9:1 and 1.1:1.

4. The cocrystal according to claim 2 wherein the cocrystal has a differential scanning calorimetry (DSC) thermogram comprising an endothermic peak at about 181.69° C.

5. The cocrystal according to claim 2 wherein the cocrystal is characterized by showing an X-ray powder diffraction pattern comprising 2θ° peaks at 6.99, 13.29, 13.42, 14.02, 17.82±0.20 2θ°, wherein the X-ray diffraction is measured using a CuKα radiation.

6. The cocrystal according to claim 1 wherein the cocrystal forming compound is urea.

7. The cocrystal according to claim 6 wherein the molar ratio of (1R,3S)-3-(5-cyano-4-phenyl-1,3-thiazol-2-ylcarbamoyl) cyclopentane carboxylic acid to urea in said cocrystal is comprised between 0.9:1 and 1.1:1.

8. The cocrystal according to claim 6 wherein the cocrystal has a differential scanning calorimetry (DSC) thermogram comprising an endothermic peak at about 197.7° C.

9. The cocrystal according to claim 6 wherein the cocrystal is characterized by showing an X-ray powder diffraction pattern comprising 2θ° peaks at 8.32, 8.82, 13.86, 15.60, 16.47, 24.86±0.20 2θ°, wherein the X-ray diffraction is measured using a CuKα radiation.

10. The cocrystal according to claim 1 wherein the cocrystal forming compound is nicotinamide.

11. The cocrystal according to claim 10 wherein the molar ratio of (1R,3S)-3-(5-cyano-4-phenyl-1,3-thiazol-2-ylcarbamoyl) cyclopentane carboxylic acid to nicotinamide is said cocrystal is comprised between 0.9:1 and 1.1:1.

12. The cocrystal according to claim 10 wherein the cocrystal has a differential scanning calorimetry (DSC) thermogram comprising an endothermic peak at about 189.55° C.

13. The cocrystal according to claim 10 wherein the cocrystal is characterized by showing an X-ray powder diffraction pattern comprising 2θ° peaks at 6.40, 8.54, 11.75, 17.29, 20.88, 23.66±0.20 2θ°, wherein the X-ray diffraction is measured using a CuKα radiation.

14. A process for the preparation of the cocrystal according to claim 1, comprising:
 a) contacting (1R,3S)-3-(5-cyano-4-phenyl-1,3-thiazol-2-ylcarbamoyl) cyclopentane carboxylic acid and a cocrystal forming compound selected from the group consisting of gentisic acid, urea and nicotinamide in the presence of a liquid, and,
 b) isolating said cocrystal.

15. The process according to claim 14 wherein the liquid is selected from the group consisting of water, methanol, ethanol, isopropanol, propanol, butanol, acetonitrile, ethyl acetate, i-butyl acetate, propan-2-one (acetone), methyl-isobutyl-ketone (MIBK), tetrahydrofuran (THF), 1,4-dioxane, dichloromethane (DCM), p-xylene, diethyl ether, methyl tert-butyl ether (TMBE) and heptane, and mixtures of thereof.

16. A combination product comprising the cocrystal according to claim 1 and one or more therapeutic agents selected from the group consisting of angiotensin converting enzyme inhibitors, angiotensin receptor antagonists, statins, beta-blockers, calcium antagonists and diuretics.

17. A pharmaceutical composition comprising the cocrystal according to claim 1 and a pharmaceutically acceptable excipient.

18. A method for the treatment of a disease known to ameliorate by A1 adenosine receptor antagonism, said method comprising administering the cocrystal according to claim 1 to a patient in need thereof.

19. The method according to claim 18 wherein the disease known to ameliorate by $A_1$ adenosine receptor antagonism is selected from the group consisting of hypertension, heart failure, ischemia, supraventricular arrhythmia, acute renal failure, myocardial reperfusion injury, asthma, allergic reactions including rhinitis and urticaria, scleroderma and autoimmune diseases.

20. The cocrystal according to claim 2 wherein the molar ratio of (1R,3S)-3-(5-cyano-4-phenyl-1,3-thiazol-2-ylcarbamoyl) cyclopentane carboxylic acid to gentisic acid in said cocrystal is 1:1.

* * * * *